United States Patent
Kishishita et al.

(10) Patent No.: US 11,408,019 B2
(45) Date of Patent: Aug. 9, 2022

(54) ALPHA-GLUCAN MIXTURE, ITS PREPARATION AND USES

(71) Applicant: Hayashibara Co., Ltd., Okayama (JP)

(72) Inventors: Seiichiro Kishishita, Okayama (JP); Shoko Kanashima, Okayama (JP); Manabu Miyata, Okayama (JP); Takuo Yamamoto, Okayama (JP); Katsuhiko Hino, Okayama (JP); Tomoyuki Nishimoto, Okayama (JP)

(73) Assignee: HAYASHIBARA CO., LTD., Okayama (JP)

( * ) Notice: Subject to any disclaimer, the term of this patent is extended or adjusted under 35 U.S.C. 154(b) by 317 days.

(21) Appl. No.: 15/780,706

(22) PCT Filed: Dec. 2, 2016

(86) PCT No.: PCT/JP2016/085946
§ 371 (c)(1),
(2) Date: Jun. 1, 2018

(87) PCT Pub. No.: WO2017/094895
PCT Pub. Date: Jun. 8, 2017

(65) Prior Publication Data
US 2018/0346949 A1    Dec. 6, 2018

(30) Foreign Application Priority Data

Dec. 4, 2015  (JP) .............. JP2015-237947

(51) Int. Cl.
| | |
|---|---|
| C12P 19/04 | (2006.01) |
| C12P 19/14 | (2006.01) |
| A23P 20/10 | (2016.01) |
| A23P 30/10 | (2016.01) |
| A23L 7/109 | (2016.01) |
| A23L 5/00 | (2016.01) |
| A61K 47/36 | (2006.01) |
| A23L 29/00 | (2016.01) |
| A61K 9/20 | (2006.01) |
| A23L 29/20 | (2016.01) |
| C08J 5/18 | (2006.01) |
| A23L 29/30 | (2016.01) |
| C08B 37/00 | (2006.01) |
| A23L 29/269 | (2016.01) |
| C12P 19/18 | (2006.01) |
| A23B 5/06 | (2006.01) |

(52) U.S. Cl.
CPC .............. *C12P 19/04* (2013.01); *A23L 5/00* (2016.08); *A23L 7/109* (2016.08); *A23L 29/00* (2016.08); *A23L 29/20* (2016.08); *A23L 29/269* (2016.08); *A23L 29/35* (2016.08); *A23P 20/105* (2016.08); *A23P 30/10* (2016.08); *A61K 9/20* (2013.01); *A61K 47/36* (2013.01); *C08B 37/0009* (2013.01); *C08J 5/18* (2013.01); *C12P 19/14* (2013.01); *A23B 5/06* (2013.01); *C08J 2305/00* (2013.01); *C12P 19/18* (2013.01); *C12Y 302/01094* (2013.01)

(58) Field of Classification Search
CPC .......... B21B 1/08; B21D 53/88; B21D 5/086; B23K 2101/006; C12P 19/04; C12P 19/14; C12P 19/18; A23L 29/269; A23L 7/109; C12Y 302/01094
USPC ........................................................ 426/573
See application file for complete search history.

(56) References Cited

U.S. PATENT DOCUMENTS

| | | | |
|---|---|---|---|
| 5,482,560 A | 1/1996 | Ammeraal et al. | |
| 2004/0014961 A1 | 1/2004 | Baker et al. | |
| 2006/0257977 A1* | 11/2006 | Hamaker | C12Y 302/01001 435/96 |
| 2009/0022872 A1* | 1/2009 | Nishimoto | A61K 9/0056 426/590 |

(Continued)

FOREIGN PATENT DOCUMENTS

| | | |
|---|---|---|
| JP | S57155969 A | 9/1982 |
| JP | 2008079525 A | 4/2008 |

(Continued)

OTHER PUBLICATIONS

Denpun kara Koso no Chikara de Tsukuru Atarashii Suiyosei Shokubutsu Sen'i "Isomaltodextrin"—Isomaltodextrin: A novel water-soluble dietary fiber produced from starch using enzymatic activity (URL:https://www.alic.go.jp/joho-d/joho08_000580.html [retrieval date: Apr. 10, 2019]—english abstract.
F. Avaltroni et al. "Maltodextrin molecular weight distribution influence on the glass transition temperature and viscosity in aqueous solutions" Carbohydrate Polymers, vol. 58, No. 3, pp. 323-334, 2004.

(Continued)

*Primary Examiner* — Jyoti Chawla
(74) *Attorney, Agent, or Firm* — Browdy and Neimark, PLLC

(57) ABSTRACT

An object of the present invention is to provide an α-glucan mixture in a preferable molecular weight range, which can be made into a transparent film with advantageous strength and water solubility when an edible film is made by using the α-glucan mixture without adding any plasticizer.
The above object is solved by providing an α-glucan mixture, which is obtainable by a process comprising the steps of gelatinizing waxy starch and liquefying the resulting gelatinized waxy starch by allowing an amylase to act on it, having the following characteristics (1) and (2):
(1) having the weight average molecular weight (Mw) in a range of 150 kDa to 3,000 kDa; and
(2) having the value of dividing weight average molecular weight (Mw) with number average molecular weight (Mn), Mw/Mn, of 35.1 or lower.

18 Claims, No Drawings

(56) References Cited

U.S. PATENT DOCUMENTS

| | | | |
|---|---|---|---|
| 2010/0120710 A1* | 5/2010 | Watanabe | A61Q 11/00 514/54 |
| 2013/0011884 A1* | 1/2013 | Ichihara | A23L 29/212 435/101 |
| 2013/0065293 A1* | 3/2013 | Watanabe | A61K 31/718 435/193 |
| 2014/0326166 A1 | 11/2014 | Mesnager et al. | |

FOREIGN PATENT DOCUMENTS

| | | |
|---|---|---|
| WO | 2001/16348 A | 3/2001 |
| WO | 2004/066955 A2 | 8/2004 |
| WO | 2008044586 A1 | 4/2008 |
| WO | 2008044588 A1 | 4/2008 |
| WO | 2008136331 A1 | 11/2008 |

OTHER PUBLICATIONS

"Product Specification Sheet of GLUCIDEX® 2" Roquette Company website, Jan. 23, 2019, Retrieved from the Internet: URL: https://www.roquette.com/food-nutrition-glucidex-2-waxy-corn-maltodextrin [retrieved on Jun. 4, 2019].

"GLUCIDEX® 2 Waxy Corn Maltodextrin—Food Nutrition | Roquette", Retrieved from the Internet: URL: https://www.roquette.com/food-nutrition-glucidex-2-waxy-corn-maltodextrin [retrieved on Jun. 4, 2019].

Gonnissen et al., Effect of maltodextrin and superdisintegrant in directly compressible powder mixtures prepared via co-spray drying, European Journal of Pharmaceutics and Biopharmaceutics, 68:277-282 (2008).

\* cited by examiner

ALPHA-GLUCAN MIXTURE, ITS PREPARATION AND USES

TECHNICAL FIELD

The present invention relates to an α-glucan mixture, its preparation and uses, particularly, to an α-glucan mixture having an advantageous applicability as a material of edible films, its preparation and uses.

BACKGROUND ART

Edible films are mainly used for the purpose of keeping a quality (particularly, freshness) of foods and the convenience of handling. Starches and those derivatives; carbohydrates such as alginic acid, pectin, arabic gum, and the like; proteins such as gelatin, casein, soy proteins, milk proteins, gluten, zein, and the like; were practically used as materials of edible films. Sometimes, lipids such as paraffin, Carnauba wax, beeswax, Candellila wax, polyethylene wax, monoglycerides of various fatty acids, and the like; resins such as shellac, rosin, copal, and the like were used as other materials of edible films. Representative edible films include wafer paper produced from starches, casing of sausage produced from collagen, microcapsules of flavors, soft capsules produced from gelatin, etc. Pullulan films and carrageenan films are used as relatively new edible films.

Wafer paper which has been widely used as an edible film is produced by making gelatinized starch, obtainable by gelatinizing potato starch, into a thin film, and has been used as an auxiliary product for wrapping and drinking medicines. However, since wafer paper is produced from gelatinized starch with a relatively high viscosity, it is required that the starch concentration of the material solution for film is controlled to a relatively low concentration. Accordingly, there is a problem in wafer paper that the film is thin in thickness and lacks strength. Gelatinized starch is produced to provide solubility in water to the material starch without reducing the molecular weight, and the adhesive and thickening properties of starch can be effectively used. However, there are problems that gelatinized starch has a relatively high viscosity, can be hardly handled, and easily forms insoluble precipitates by retrogradation.

While, partial starch hydrolyzate (dextrin) is formed by hydrolyzing starch material to saccharides with relatively low molecular weight by acids, alkali or enzymes in the course of the production. Although dextrin has a satisfactory solubility in water, there is a problem that it is hard to shape into a film with a satisfactory strength because the viscosity is lowered. Further, there is a problem that dextrin causes the browning by its Maillard reaction when it is heated in a mixed form with proteins, amino acids, and the like, because dextrin has a relatively increased reducing power by the hydrolysis.

In many cases, a starch-based edible film is produced by incorporating with a plasticizer such as glycerol, sorbitol, sorbitol ester, etc., for the purpose of improving fragility at a low temperature and increasing elasticity. However, it has been reported that the strength of the film may be remarkably deteriorated by admixing plasticizers such as polyalcohols, and the like (refer to Patent Literature 1).

Under these circumstances, it would be extremely useful if an edible material, having benefits of both gelatinized starch and dextrin, i.e., adequate molecular weight, viscosity, and solubility in cold water, and which can be made into a film with advantageous transparency, strength, and solubility without adding any plasticizer, can be provided.

PRIOR ART LITERATURE

Patent Literature

[Patent Literature 1] Japanese Patent Kokai No. 2008-79525

DISCLOSURE OF INVENTION

Object of the Invention

The object of the present invention is to provide an edible material having a preferable molecular weight, viscosity, and solubility in cold water, which can be made into a film with advantageous transparency, strength, and solubility in water when it was made into a film without adding any plasticizer, and its preparation and uses.

Means to Attain the Object

To solve the above objects, the present inventors continued studying by repeated trial and error. As the results, the present inventors found that a novel α-glucan mixture having a preferable molecular weight range and viscosity can be obtained by gelatinizing waxy starch and liquefying the resulting gelatinized starch by allowing a small amount of amylase to act on it. Further, the present inventors found that an edible film with advantageous transparency, strength, and solubility in water can be produced in a low cost by using the α-glucan mixture without adding any plasticizer. Thus, they accomplished the present invention.

The present invention solves the above objects by providing an α-glucan mixture, which is obtainable by a process comprising the steps of gelatinizing waxy starch and liquefying the resulting gelatinized waxy starch by allowing an amylase to act on it, having the following characteristics (1) and (2):

(1) having the weight average molecular weight (Mw) in a range of 150 kDa to 3,000 kDa; and
(2) having the value of dividing weight average molecular weight (Mw) with number average molecular weight (Mn), Mw/Mn, of 35.1 or lower.

The present inventors also found that an α-glucan mixture containing α-glucan having an isomaltose structure at the non-reducing end can be obtained by allowing an enzyme, having an activity of acting on partial starch hydrolyzate and catalyzing α-1,6 transglucosylation to the non-reducing end glucose residue, to act on the above α-glucan mixture. The present inventors found that the resulting α-glucan mixture had a merit of showing remarkable tolerance for retrogradation in addition to the useful properties as the material of edible film described above.

The present invention also solves the above objects by providing an α-glucan mixture, having the above characteristics (1) and (2) and further containing α-glucan having an isomaltose structure at the non-reducing end.

Further, the present invention solves the above objects by providing an edible film obtainable by the steps of molding the above α-glucan mixture without adding any plasticizer and drying the resultant. The edible film of the present invention has an advantageous characteristic of exhibiting a rapture strength of piercing of 2.0 N/mm$^2$ or higher when analyzed on a piercing test for rupture strength using an adaptor with a sectional area of 1 mm$^2$.

Furthermore, the present invention solves the above objects by providing foods, cosmetics, pharmaceuticals, and industrial products, containing the above α-glucan mixture.

Effect of the Invention

The α-glucan mixture of the present invention has merits of having adequate molecular weight and viscosity, a relatively high solubility in water, and ease of handling. Edible films with satisfactory transparency, strength, and solubility in water can be obtained without adding any plasticizer by preparing films by using the α-glucan mixture of the present invention as a material. Therefore, the α-glucan mixture of the present invention can be advantageously used as a material for edible films for foods. Further, the α-glucan mixture of the present invention is useful as a material for foods, industrial products, cosmetics, and pharmaceuticals.

The α-glucan mixture, containing α-glucan having an isomaltose structure at the non-reducing end, of the present invention has a remarkable tolerance for retrogradation in addition to the above physical properties and applicability as a material of an edible film. Therefore, the above α-glucan mixture can be more advantageously used as a material of edible films and materials of foods, industrial products, cosmetics, and pharmaceuticals.

MODE FOR CARRYING OUT THE INVENTION

1. Definition of Terms

Throughout the specification, the following terms mean as follows:

<Waxy Starch>

Generally, it has been known that starches are in a form of a mixture of amylose, having a structure that a constitutive saccharide, glucose, are linearly bound via α-1,4 linkages, and amylopectin, having a structure that amylose is branched at the various point of inner glucose via α-1,6 linkages. "Waxy starch" as referred to as in the present specification means starches obtainable from waxy plants, for example, waxy-rice, -barley, -wheat, -hare, -corn, -crime, -millet, and -fish. Waxy starches are known to have a characteristic that they hardly contain amylose and substantially constructed by amylopectin only. Among them, waxy corn starch is a starch obtainable from waxy corn and most commonly used because it can be easily gelatinized and the resulting gel exhibits advantageous storage stability. Accordingly, waxy corn starch is advantageously used as a material of α-glucan mixture of the present invention.

<Gelatinization>

"Gelatinization" as referred to as in the present specification means a phenomenon that hydrogen bonds of starch particles are destroyed and starch particles are irreversibly swelled (or hydrated, dissolved) when starch particles are heated in the presence of water. Starches lose their crystalline nature and biurefringence by gelatinization and the viscosity and reactivity to enzymes (amylases) and chemicals are rapidly increased. Gelatinization may be also called to "Alpha-ka" in Japanese.

<Liquefaction>

"Liquefaction" as referred to as in the present specification means a step of liquefying the gelatinized starch obtained above by partially hydrolyzing it by allowing amylase to act on the gelatinized starch. Liquefied starch (α-glucan mixture) obtained by liquefying the gelatinized starch shows relatively lower molecular weight and lower viscosity with the increase of the degree of hydrolysis.

<Mw/Mn (a Value of Dividing Weight Average Molecular Weight with Number Average Molecular Weight)>

"Mw/Mn" as referred to as in the present invention means a value of dividing weight average molecular weight (Mw) with number average molecular weight (Mn). Mw/Mn is an index indicating spread of molecular weight distribution of α-glucan mixture. A larger value of Mw/Mn means that the molecular species extend over a broad molecular weight range. The closer the value of Mw/Mn is to 1, means that the molecular species are homogeneous in their molecular weights. Mw/Mn can be calculated by the steps of subjecting test sample to gel-filtration high performance liquid chromatography (gel-filtration HPLC) and analyzing the chromatogram by a software for molecular weight distribution and determining Mw and Mn.

<Solubility in Cold Water>

"Solubility in cold water" as referred to as in the present specification means a property of providing a homogeneous aqueous solution by dissolving completely within 15 min when judged by the steps of dissolving a test sample into deionized water to give a solid concentration of 20% by weight, stirring at a solution temperature of 30° C. and judging the degree of dissolution by visual observation. An α-glucan mixture showing the solubility in cold water has a merit of ease of handling because it is not necessary to dissolve the α-glucan mixture by heating when it is incorporated into various compositions.

<Retrogradation>

"Retrogradation" as referred to as in the present specification means a phenomenon that gelatinized starch or liquefied starch is changed with time to water-insoluble form as in the case of natural starches. The retrogradation of starch is a stage change of naturally associating starch molecules and changing to a partially tight aggregate. It was considered that the association of molecules was caused by hydrogen bonds of hydroxyl groups of glucose residues. When time passes, the phenomenon that white turbidity is formed from gelatinized starch or liquefied starch is observed. The white turbidity is caused by the retrogradation and insolubilization of gelatinized starch or liquefied starch. It is well-known that starch is constructed by amylose and amylopectin and linear amylose with no branch easily shows retrogradation.

<Film>

"Film" as referred to as in the present specification means a thin film obtained by molding a polysaccharide having a relatively high molecular weight, particularly, starch or α-glucan mixture, and that keeping the thin film structure after molding. Usually, it has been said that a film means one having a thickness of 250 μm or lower. A film is often provided in a form of a roll that a long product is rolled up. Even in the same product, a product with thin in thickness and in a form of roll is sometimes called as "film", and a product with thick in thickness and in a form of cut into an appropriate size is sometimes called as "sheet". In the following Experiments, a film sample not containing any plasticizer was prepared by the steps of dissolving a test sample into deionized water to give an aqueous solution with a solid concentration of 30% by weight, dropping and casting the adequate amount of the solution on a polyethylene terephthalate plate using "Model YBA", a baker applicator, commercialized by Yoshimitsu Seiki, Japan, and drying it at an ambient temperature for overnight.

<Rupture Strength of Piercing>

"Rupture strength of piercing" as referred to as in the present specification means a stress measured when a film is subjected to the piercing test for rupture strength and the rupture is occurred. In the following Experiments, each film sample was cut into a circle with a diameter of 20 mm, and adjusted the humidity by keeping at an ambient temperature under a relative humidity of 52.8% for overnight, and then subjected to the piercing test for rupture strength conducted with "Rheometer CR-500DX" commercialized by Sun Scientific Co, Ltd., Tokyo Japan, installed with an adaptor for piercing test with a cross-section area of 1 mm² in such a manner of perpendicularly pressing the adaptor on the center of the film, fixed on the apparatus at a velocity of 50 mm/min to cause the rapture, followed by determining the stress for rupture strength of piercing. The rupture strengths of piercing of 10 sheets each of film were determined and the values were averaged. The averaged value was used as the rupture strengths of piercing of the film sample.

<α-Glucosyltransferase>

"α-Glucosyltransferase" (hereinafter, abbreviated as "α-GTase" in this specification) as referred to as in the present specification means an enzyme having an activity of acting on partially starch hydrolyzate and catalyzing α-1,6 transglucosylation to the non-reducing end glucose residue. An α-glucan mixture having an isomaltose structure at the non-reducing end can be obtained by allowing the α-GTase to act on α-glucan mixture. The α-GTase includes, for example, α-glucosidase, α-glucosyltransferase, dextrin dextranase, etc.

<Isomaltodextranase Digestion>

"Isomaltodextranase digestion" as referred to as in the present specification means a method of allowing isomaltodextranase to act on an aqueous solution of a test sample and hydrolyzing the linkage adjacent to reducing end side of isomaltose structure in the test sample. Isomaltodextranase (EC 3.2.1.94, hereinafter, abbreviated as "IDase" in this specification) is an enzyme capable of hydrolyzing α-1,2, α-1,3, α-1,4, and α-1,6 linkages as far as the linkage is adjacent to reducing end side of isomaltose structure in a glucan such as dextran. Therefore, it can be investigated whether the test sample contains α-glucan having an isomaltose structure at the non-reducing end or not by the steps of allowing IDase to act on the test sample, subjecting the resulting digest to HPLC analysis, and determining that isomaltose is observed in the digest or not. In the following Experiments, the isomaltose content of a test sample was measured by the steps of dissolving the test sample into water to give a concentration of 1% (w/v), adding 100 units/g-solid test sample of IDase specimen derived from *Arthrobacter globiformis*, prepared by Hayashibara Co., Ltd., Okayama, Japan, allowing the enzyme to act on the aqueous solution of the test sample, and subjecting the resulting digest to the HPLC analysis for determining saccharide composition, using the following conditions.

(Conditions for HPLC for Saccharide Composition Analysis)

Column: MCI GEL CK04SS (commercialized by Mitsubishi Chemical Industries Corp., Tokyo, Japan) (two columns were connected in series)
 Eluent: water
 Column temperature: 80° C.
 Flow rate: 0.4 mL/min
 Detection: "RID-10A", a reflective index detector commercialized by Shimadzu Corporation, Kyoto, Japan <Dextrose Equivalent (DE)>

"Dextrose equivalent" as referred to as in the present specification is an index of indicating a degree of progress of hydrolysis for starchy saccharides (partial starch hydrolyzates) obtainable by hydrolyzing starch using acids or enzymes, and means a value represented by the following equation. Dextrose equivalent (hereinafter, simply abbreviated as "DE" in this specification) is a relative scale that the reducing power of D-glucose (dextrose) is assumed to be 100. A glucan mixture with the value close to zero shows a low degree of hydrolysis and exhibits properties similar to starch, and that with the value close to 100 shows a high degree of hydrolysis and exhibits properties similar to glucose.

$$\text{Dextrose equivalent } (DE) = \frac{\text{Amount of reducing sugar (as glucose)}}{\text{Total amount of solid}} \times 100 \quad \text{[Equation 1]}$$

The amount of reducing sugar described above is determined by using D-glucose as standard substance according to the conventional improved Park-Johnson method (refer to Hizukuri et al., *Carbohydrate Research*, Vol. 94, pp 205-213 (1981)). The total amount of solid is determined by the conventional drying method.

<Amylose Content>

Since each starch has different amylose content depending on the species of starch such as corn starch, potato starch, cassava starch, and the like, an amylose content can be used as one of the index for specifying the starch species. "Amylose content" as referred to as in the present specification means the amylose content of a test sample, measured based on a color reaction of amylose and iodine according to the method for determining amylose content described in the standard measurement method of the Ministry of Agriculture, Forestry and Fisheries notification No. 332, and said test sample is starch, its partial hydrolyzate (α-glucan mixture) formed by the digestion of amylase, or starchy substances including an α-glucan mixture obtainable by allowing α-GTase to act on them. The concrete method for determining amylase content is composed by the following steps:

(1) 100 mg of an analytical sample is admixed with 1 mL of ethanol and 9 mL of 1 M sodium hydroxide solution, heated in boiling water for 10 min, and then added water to prepare a test sample solution with a volume of exactly 100 mL;

(2) successively, 5 mL of the resulting test sample solution and 1 mL of 1 M acetic acid solution are mixed, and then 2 mL of iodine-potassium iodine solution is added and mixed, and further added water to obtain the measurement solution with a volume of 100 mL;

(3) after the temperature is adjusted by keeping the measurement solution at 27° C. for 30 min, an absorbance at a wavelength of 620 nm of the measurement solution is measured using a spectrophotometer; and (4) the amylose content is calculated by determining the amount of amylose based on the value of the absorbance and a calibration curve which is similarly measured and prepared for the amylose standard solution prepared using a reagent grade amylose.

2. The α-Glucan Mixture of the Present Invention

The α-glucan mixture of the present invention is obtainable by a process comprising the steps of gelatinizing waxy starch and liquefying the resulting gelatinized waxy starch by allowing an amylase to act on it, and has the following characteristics (1) and (2):

(1) having Mw in a range of 150 kDa to 3,000 kDa; and
(2) having the value of dividing Mw with Mn, Mw/Mn, of 35.1 or lower.

The α-glucan mixture of the present invention is characterized in that it can be obtained by a process comprising the steps of gelatinizing waxy starch and liquefying the resulting gelatinized waxy starch by allowing an amylase to act on it. Waxy starch is a starch substantially composed of amylopectin having branched structures, and does not substantially contain a linear α-1,4-glucan, amylose. Waxy starch has properties of being easily gelatinized and inherently showed low retrogradation in comparison with starches containing amylose other than waxy starch, and therefore, the digested waxy starch also has the same properties. Further, waxy starch is advantageous in film-forming property (film-forming ability) in comparison with starches containing amylose other than waxy starch. Although acids can be used for liquefying gelatinized starch, a method for using an amylase is advantageous because the degree of hydrolysis can be easily controlled.

The α-glucan mixture of the present invention is characterized to have (1) Mw in a range of 150 kDa to 3,000 kDa, and, more preferably, in a range of 200 kDa to 3,000 kDa. When Mw of the α-glucan mixture is less than 150 kDa, the ratio of molecules having a small molecular weight is increased, viscosity and film-forming property (film-forming ability) is lowered and the reducing power is increased. When Mw of the α-glucan mixture is over 3,000 kDa, it is hardly dissolved in water, and hardly handled because of the high viscosity, and it is difficult to use. When a film is prepared by using such α-glucan mixture, the film lacks transparency and water solubility.

The α-glucan mixture of the present invention is characterized to have (2) the value of dividing Mw with Mn, Mw/Mn, of 35.1 or lower. When the value of Mw/Mn is over 35.1, the ratio of low-molecular weight molecules in the α-glucan mixture is increased, and the film-forming property becomes poor.

In the case of α-glucan mixture obtained by partially hydrolyzing waxy starch by amylase, the value of Mw/Mn can be controlled to a low level, usually, less than 10, preferably, less than 8, and more preferably, less than 6. On the other hand, as described in the following Experiments, an α-glucan having Mw less than 150 kDa and Mw/Mn over 35.1, which is obtained by hydrolyzing waxy corn starch by amylase, is difficult to make into a film.

The more preferred embodiment of the α-glucan mixture of the present invention is the α-glucan mixture containing α-glucan having an isomaltose structure at the non-reducing end, in addition to having the characteristics of the above (1) and (2). Such α-glucan mixtures can be obtained by further allowing an α-GTase, having activities of acting on partial starch hydrolyzate and catalyzing α-1,6 transglucosylation to the glucose residue at the non-reducing end.

In order to confirm whether the α-glucan mixture contains α-glucan having an isomaltose structure at the non-reducing end or not, it can be investigated by the steps of dissolving the α-glucan mixture into water, digesting the α-glucan mixture by allowing IDase to act on it, and measuring the isomaltose content in the digest. The α-glucan mixture containing α-glucan having an isomaltose structure at the non-reducing end of the present invention is characterized in that isomaltose in an amount of over 3% by weight but less than 22% by weight, on a dry solid basis of the digest, is formed from the α-glucan mixture by IDase digestion.

The α-glucan mixture of the present invention containing α-glucan having an isomaltose structure at the non-reducing end, has a property of being hardly showed retrogradation in comparison with an α-glucan mixture (partial starch hydrolyzate) and a linear α-1,4-glucan having a structure of binding glucose molecule via α-1,4 linkages because it contains α-glucan having an isomaltose structure at the non-reducing end, which is a specific structure not inherently present in hydrolyzate of starch. Among the α-glucan mixture, containing α-glucan having an isomaltose structure at the non-reducing end, of the present invention, the α-glucan mixture which shows the isomaltose content of over 3% by weight but less than 22% by weight, on a dry solid basis of digest, when digested using IDase has a tolerance for retrogradation that no white turbidity due to the retrogradation is observed when an aqueous solution of the α-glucan mixture with a solid concentration of 30% by weight is kept at 6° C. for one-week. Therefore, the α-glucan mixture of the present invention has an advantage that it can be stored in the form of aqueous solution with a relatively high concentration before use.

As described later in the following Experiments, even in the case of the α-glucan mixture obtained by allowing amylase to act on waxy starch, the α-glucan mixture showing the isomaltose content of 3% by weight or lower/solid of the IDase digest is not significantly different in the tolerance for retrogradation in comparison with α-glucan with no isomaltose structure at the non-reducing end. The α-glucan mixture showing the isomaltose content of 22% by weight or higher/solid of the IDase digest has an increased tolerance for retrogradation, however, the Mw/Mn is increased to over 35.1, the film-forming property is reduced, and the α-glucan mixture tends to being hardly made into films. In the case of the α-glucan mixture containing α-glucan having an isomaltose structure at the non-reducing end, it is inevitable to increase the value of Mw/Mn because the α-glucan mixture is produced by using α-GTase in addition to amylase and the structure of the formed respective α-glucan molecule is remarkably varied. Therefore, in the case of an α-glucan mixture produced by using amylase and α-GTase, it is preferable to control the value of Mw/Mn to, usually, 35.1 or lower, and preferably, 25 or lower. When the value of Mw/Mn of the α-glucan mixture is over 35.1, the content of low molecular weight α-glucan is increased and it causes a problem in the film forming.

DE of the α-glucan mixture of the present invention is not particularly restricted. DE can be used as an index of the degree of hydrolysis of waxy starch and also as an index of Mw defined above. It varies depending on the application of the α-glucan mixture, in the cases of heating in a mixed form with proteins or amino acids, the α-glucan mixture which hardly causes discoloration or browning by Maillard reaction is desired. In such a case, an α-glucan mixture with a low DE is preferable. In the case of an α-glucan mixture obtained by partially hydrolyzing waxy starch by amylase, DE can be controlled to a low level, usually, lower than 1.0, preferably, 0.8 or lower, more preferably, 0.62 or lower. As described later in the following Experiments, an α-glucan mixture obtained by hydrolyzing waxy starch by amylase to give the DE value of over 1.0, Mw of the α-glucan mixture is lowered to less than 150 kDa and the α-glucan mixture is hardly made into a film. On the other hand, in the case of the α-glucan mixture containing α-glucan having an isomaltose structure at the non-reducing end, produced by the steps of partially hydrolyzing waxy starch by amylase and successively allowing α-GTase to act on the resulting hydrolyzate, it is inevitable to slightly increase DE because α-GTase is used in addition to amylase. Therefore, in the case of an α-glucan mixture produced by using amylase and α-GTase, it is preferable to control the DE to, usually, 2.0 or lower, preferably, 1.8 or lower, and more preferably, 1.6 or lower. In the case of the α-glucan mixture containing α-glucan having isomaltose structure at the non-reducing end, Mw of the α-glucan mixture is kept to be 300 kDa or higher even in the case of the DE being over 2.0. However, when the DE of the α-glucan mixture is over 2.0, the Mw/Mn (degree of dispersion) is increased to 35.1, and as a result, it causes a problem in the film forming.

Waxy starch used as a material of the α-glucan mixture of the present invention is not restricted by its origin plant as far as the α-glucan mixture has desired properties. Waxy corn starch is preferably used as a waxy starch for producing the α-glucan mixture of the present invention because it is produced in large scale, can be readily available, and is widely used. Generally, it has been said that waxy starch does not substantially contain a linear glucose polymer, amylose, having a structure of binding glucose via α-1,4 linkage. However, waxy starch shows the amylose content of, usually, 15% by weight or lower in the aforementioned method for determining amylose content based on the iodine coloring method. The value of the amylose content of the α-glucan mixture of the present invention, obtained by the step of hydrolyzing a material waxy starch by amylase, or by the steps of hydrolyzing a material waxy starch by amylase and further transferring α-glucosyl residue to the resulting hydrolyzate, is varied depending on the species of waxy starch used as a material. The α-glucan mixture of the present invention usually shows the value of the amylose content of 15% by weight or lower.

The α-glucan mixture of the present invention has solubility in cold water. The α-glucan mixture is completely dissolved in water and can be made into a homogeneous solution when it is added to deionized water to give a solid concentration of 20% by weight and stirred at 30° C.

The α-glucan mixture of the present invention is suitable as a material of edible films, and can be made into a film using the aqueous solution of the α-glucan mixture by conventional method without using any plasticizer. The film prepared by using the α-glucan mixture of the present invention as a material has satisfactory transparency and solubility in water. The film adjusted in a thickness of 40 µm or higher usually exhibits a rapture strength of piercing of 2.0 N/mm² or higher, preferably, 2.5 N/mm² or higher, and more preferably, 3.0 N/mm² or higher, when a rapture strength of piercing test is performed using a piercing test adapter having a cross-sectional area of 1 mm². As described later in the following Experiments, the above value of the rapture strength of piercing is an equal to or slightly lower level of that of a pullulan film with the same thickness obtained by molding pullulan, which has been widely used as a material of edible film in the art, by the same method and same conditions. The fact indicates that the α-glucan mixture of the present invention can be used for the same applications as pullulan.

3. The Process for Producing the α-Glucan Mixture of the Present Invention

The process for producing α-glucan mixture of the present invention comprises the steps of gelatinizing waxy starch, allowing an amylase to act on the gelatinized starch, and forming the α-glucan mixture having Mw in a range of 150 to 3,000 kDa. The process is not particularly restricted by the origin of waxy starch, conditions for the gelatinization, kind and the origin of amylase as long as the α-glucan mixture having the following characteristics (1) and (2) can be obtained:

(1) having Mw in a range of 150 kDa to 3,000 kDa; and
(2) having the value of dividing Mw with Mn, Mw/Mn, of 35.1 or lower.

The gelatinization of waxy starch can be carried out by a conventional method of heating an aqueous suspension containing waxy starch. Specifically, a method for indirectly heating the aqueous suspension containing waxy starch in a jacketed reactor, that for directly heating the aqueous suspension containing waxy starch by mixing steam, and a method for heating the aqueous suspension containing waxy starch on a hot roll of the drum dryer can be used. The gelatinized waxy starch is liquefied by adding amylase for hydrolyzing. Nowadays, a method of gelatinizing and liquefying starch simultaneously is generally carried out by the steps of previously adding amylase to a starch suspension and heating the resulting mixture. The methods of gelatinization and liquefaction of starch can be appropriately selected from conventional methods and carried out, usually, either a batch system or a continuous system.

A commercially available thermostable liquefying-type α-amylases are preferably used for liquefying the gelatinization starch. The commercially available thermostable α-amylase for liquefaction includes, for example, "Spitase HK" commercialized by Nagase ChemteX Corporation, Osaka, Japan, "Termamyl 60L" commercialized by Novozymes Japan Co., Ltd., Tokyo, Japan, "Amylase AD Amano" commercialized by Amano Enzyme Inc., Aichi, Japan, "Kleistase T10S" commercialized by Amano Enzyme Inc., Aichi, Japan, and "Sumizyme L" commercialized by Shin Nihon Chemical Co., Ltd., Aichi, Japan.

In the process for producing the α-glucan mixture of the present invention, concentration of waxy starch as a material, an amylase used for liquefying (partially hydrolyzing), the amount of the amylase, reaction temperature and reaction time for the gelatinization and liquefaction, the temperature for stopping of the reaction, the system of the reaction (batch system or continuous system) and etc. can be arbitrarily selected according to the physical properties required for the α-glucan mixture of the present invention. The preferable concentration of waxy starch as a material is, usually, 10% by weight or higher, desirably, about 20 to 50% by weight, and more desirably, 30 to 35% by weight. As described in the following Experiments, in order to produce the α-glucan mixture of the present invention, it is necessary to control the Mw of the liquefied waxy starch (α-glucan mixture) to be in a range of 150 kDa to 3,000 kDa by partially hydrolyzing waxy starch by controlling the amount of the above amylase. Although the Mw of the liquefied product can be measured by gel filtration HPLC, it can be determined by measuring the DE and viscosity of the liquefied product instead of measuring Mw, by preliminary investigating the relationship between the Mw and the DE, or between the Mw and the viscosity. As described in the following Experiments, in order to control Mw of a liquefied waxy starch to be 150 kDa or higher, it is preferable to control the DE to, usually, less than 1.0, desirably, 0.62 or lower. In order to control the DE of liquefied waxy starch to a relatively low value, less than 1.0, it is preferable to terminate the gelatinization and liquefaction in as short a time as possible, and as a method of the gelatinization and liquefaction, the continuous system is more preferable than the batch system, because the method can be used for heating a starch suspension uniformly and rapidly.

The α-glucan mixture containing α-glucan having an isomaltose structure at the non-reducing end can be produced by allowing an α-GTase, having an activity of acting on partial starch hydrolyzate and transferring glucose to the non-reducing end glucose of the partial starch hydrolyzate by α-1,6 transglucosylation, to act on an α-glucan mixture obtainable by partially hydrolyzing the above waxy starch. The α-GTase is not restricted by its origin and physical properties as far as it has an activity of acting on partial starch hydrolyzate and transferring glucose to the non-reducing end glucose of the partial starch hydrolyzate by α-1,6 transglucosylation. The α-GTase having the above activity includes, for example, Transglucosidase (α-glucosidase) derived from *Aspergillus niger*, Dextrin dextranase derived from *Acetobacter capsulatum*, "α-GTase" derived from a microorganism of the genus *Bacillus* or *Arthrobacter* disclosed in WO2008/136331 applied for by the same applicant as the present application, and "α-isomaltosylglucosaccharide-forming enzyme" derived from a microorganism of the genus *Bacillus* or *Arthrobacter* disclosed in WO02/010361 applied for by the same applicant as the present application. Particularly, the α-GTase and α-isomaltosylglucosaccharide-forming enzyme, derived from a microorganism of the genus *Bacillus* or *Arthrobacter*, can be more preferably used.

The α-GTase disclosed in WO2008/136331, has an activity of acting on maltose and/or α-1,4 glucan having a glucose polymerization degree of three or higher, transferring a non-reducing end glucose residue to the non-reducing end glucose residue of the other α-1,4 glucan by mainly α-1,4 or α-1,6 transglucosylation reaction, and forming a glucan having a structure of binding glucose to the C-4 or C-6 hydroxyl group of the non-reducing end glucose residue via α-linkage. By repeating the transglucosylation reaction using the α-GTase, a branched α-glucan mixture with a complex branched structure can be produced from maltose and/or α-1,4 glucans having a glucose polymerization degree of three or higher. The α-GTase also has an activity of forming α-glucan mixture further having α-1,3-, α-1,4,6-, and α-1,3,6-linkages by catalyzing α-1,3 transglucosylation and α-1,4 or α-1,3 transglucosylation to a glucose residue bound via α-1,6 linkage in a glucan, even in a low frequency. By using the α-GTase, an isomaltose structure can be introduced to the non-reducing end of α-glucan and the α-glucan mixture containing the α-glucan having an isomaltose structure at the non-reducing end can be produced.

Alpha-GTase from a microorganism of the genus *Bacillus* or *Arthrobacter* disclosed in WO2008/136331 has the following characteristics (A) to (F):

(A) Action
Acting on maltose and/or α-1,4 glucans having a glucose polymerization degree of three or higher, catalyzing mainly α-1,4-transglucosylation or α-1,6-transglucosylation, and transferring glucose to the hydroxyl group at the C-4 or C-6 position of glucose residue at the non-reducing end;

(B) Molecular Weight
90,000±10,000 daltons when determined on SDS-polyacrylamide gel electrophoresis;

(C) Optimum Temperature
About 50° C. when reacted at pH 6.0 for 30 min;

(D) Optimum pH
About pH 6.0 when reacted at 40° C. for 30 min;

(E) Thermal Stability
Stable up to 40° C. when incubated at pH 6.0 for 60 min; and (F) pH Stability
Stable in the pH range of 4.0 to 8.0 when incubated at 4° C. for 24 hours.

"Alpha-isomaltosylglucosaccharide-forming enzyme" disclosed in WO02/010361, namely, an α-GTase has an activity of acting on maltose and/or α-1,4 glucans having a glucose polymerization degree of three or higher as substrates and forming α-glucans having a structure of binding glucose to the hydroxyl group at the C-6 position of the non-reducing end glucose residue via α-linkage, by transferring the non-reducing end glucose residue to the non-reducing end glucose residue of the other α-1,4 glucan by α-1,6 transglucosylation. This α-GTase has no activity of further transferring glucose to a glucan having an isomaltose structure at the non-reduction end, therefore, a branched α-glucan with complicated branched structure could not be produced as in the case of the aforementioned enzyme by the enzyme. However, the α-GTase can also be used for introducing an isomaltose structure into the non-reducing end of α-glucan without greatly changing Mw/Mn (dispersity), and can be used for producing the α-glucan mixture containing the α-glucan having an isomaltose structure at the non-reducing end.

"Alpha-isomaltosylglucosaccharide-forming enzyme" derived from a microorganism of the genus *Bacillus* or *Arthrobacter* disclosed in WO02/010361 has the following characteristics (G) to (M):

(G) Action
Forming a saccharide having a glucose polymerization degree of at least three and having both the α-1,6 glucosidic linkage as the linkage at the non-reducing end and the α-1,4 glucosidic linkage other than the above linkage, via the α-glucosyltransfer from a material saccharide having a glucose polymerization degree of at least two and having the α-1,4 glucosidic linkage as the linkage at the non-reducing end, without substantially increasing the reducing power of the material saccharide;

(H) Molecular Weight
About 74,000 to about 160,000 daltons when determined on SDS-PAGE (sodium dodecyl sulfate polyacrylamide gel electrophoresis);

(I) Isoelectric Point
About 3.8 to about 7.8 when determined on isoelectrophoresis using ampholine;

(J) Optimum Temperature
About 40° C. to about 50° C. when incubated at a pH of 6.0 for 60 min;
About 45° C. to about 55° C. when incubated at a pH of 6.0 for 60 min in the presence of 1 mM $Ca^{2+}$;
60° C. when incubated at a pH of 8.4 for 60 min; or
65° C. when incubated at a pH of 8.4 for 60 min in the presence of 1 mM $Ca^{2+}$;

(K) Optimum pH
About 6.0 to about 8.4 when incubated at 35° C. for 60 min;

(L) Thermal Stability
Stable in a range of about 45° C. or lower when incubated at a pH of 6.0 for 60 min,
Stable in a range of about 50° C. or lower when incubated at a pH of 6.0 for 60 min in the presence of 1 mM $Ca^{2+}$,
Stable in a range of about 55° C. or lower when incubated at a pH of 8.0 for 60 min, and
Stable in a range about 60° C. or lower when incubated at a pH of 8.0 for 60 min in the presence of 1 mM $Ca^{2+}$;

(M) pH Stability
Stable in a range of about pH 4.5 to about pH 10.0 when incubated at 4° C. for 24 hours.

The α-glucan mixture containing α-glucan having an isomaltose structure at the non-reducing end, which is obtainable by the action of α-GTase, may have a larger Mw/Mn than the α-glucan mixture used as a material and show a slightly increase DE. However, as described later in the following Experiments, the α-glucan mixture having the Mw/Mn in a range of 35.1 or lower and the DE of less than 2.8, obtainable by controlling the amount of α-GTase, is an excellent material for edible films, which can be molded into a film and used without any problem.

Although a reaction mixture containing the α-glucan mixture of the present invention, obtained by the enzyme reaction, can be used intact as an α-glucan mixture product, the reaction mixture is usually used after purification. Conventional methods for purifying saccharides can be arbitrarily selected as the purification method. For example, one or more purification methods selected from the group consisting of decoloring with activated charcoal; desalting using ion exchange resins in H— and OH-form; separation using organic solvents such as alcohol and acetone; and separation using a membrane having a suitable separability; can be arbitrarily used.

The α-glucan mixture of the present invention is in a form of a mixture of α-glucans having relatively large molecular weights, and hardly contains low-molecular oligosaccharides. Therefore, it is not necessary to purify the reaction product by column chromatography. However, the reaction product can be arbitrary fractionated according to the object of the application. When ion-exchange chromatography is used for fractionating the α-glucan mixture, column chromatography using a strongly acidic cation exchange resin, described in Japanese Patent Kokai Nos. 23,799/83 and 72,598/83 can be advantageously used. In such cases, any one of fixed bed, moving bed, and semi-moving bed methods can be arbitrary employed.

Although the solution of the α-glucan mixture of the present invention thus obtained can be used intact, it is desirable to make the α-glucan mixture into a powdery form by drying for the preservation and handling. Usually, various dryers such as a drum dryer, spray dryer, hot air dryer, vacuum dryer, air flow dryer, freeze dryer, and a fluidized bed dryer can be used. Optionally, the dried α-glucan mixture can be arbitrary made into powder in a specific particle size range by pulverizing, sieving, and granulating.

4. Uses of the α-Glucan Mixture of the Present Invention

The α-glucan mixture of the present invention has satisfactory suitability as a film, thus, without adding any plasticizer, it is easy to make α-glucan mixture into a film having an appropriate size and thickness by an appropriate method, and it can be advantageously used as a material for edible films. When the α-glucan mixture is made into a film, a film with satisfactory rapture strength of piercing, transparency, solubility in water, and durability in use, can be provided. Thus, the α-glucan mixture of the present invention can be advantageously used as a material for films, sheets, and coatings used in the fields of foods, cosmetics, pharmaceuticals, industrial products, etc. The α-glucan mixture of the present invention can be advantageously made into a film in combination with conventionally known plasticizers. In the case of making the α-glucan mixture of the present invention into a film or the like, a nonionic surfactant such as sucrose fatty acid ester can be used as a remover.

As described later in Experiment (Reference Experiment), a film with a thickness of 40 to 50 μm prepared by using the α-glucan mixture of the present invention has a rapture strength of piercing comparable to that of the pullulan film, prepared by the same method and under the same condition to be a film with the same thickness by using pullulan which has been widely used as a material of edible films.

A powder of the α-glucan mixture of the present invention has white appearance and satisfactory free-flowing-ability, and exhibits a preferable solubility in water, thus, in addition to the use for the material of edible film described above, it can be used for various uses The α-glucan mixture of the present invention exhibits various properties such as adhesion property, osmotic pressure-controlling property, excipient property, gloss-imparting property, moisture-retaining property, viscosity-imparting property, crystallization-inhibiting property for other saccharides, etc. Therefore, the α-glucan mixture of the present invention can be advantageously used as quality-improving agent, stabilizer, excipient, etc., for various compositions such as foods, favorite products, feeds, baits, cosmetics, pharmaceuticals, and industrial products.

Depending on use, the α-glucan mixture of the present invention can be arbitrarily used after mixing with one or more ingredients, generally used in the fields of foods, cosmetics, pharmaceuticals, industrial products, selected from the group consisting of other materials, for example, polysaccharides, bulking agents, excipients/adjuvants, fillers, viscosity-imparting agents, surfactants, foaming agents, antifoam agents, pH-controlling agents, stabilizers, flame retardants, mold release agents, antiseptics, colors, flavors, nutrients, preferences including tobaccos, taste-imparting agents, medicines, and physiologically active substances.

The α-glucan mixture of the present invention can be used in combination with sweeteners, for example, powdery syrup, glucose, fructose, isomerized sugar, sucrose, maltose, trehalose, honey, maple sugar, sorbitol, maltitol, dihydrochalcone, stevioside, α-glycosyl stevioside, sweetener of *Momordica grosvenori*, glycyrrhizin, thaumatin, sucralose, L-aspartyl L-phenylalanine methyl ester, saccharine, glycine and alanine; and fillers such as dextrin, starch, pullulan, dextran, and lactose. Further, powdery products of the α-glucan mixture of the present invention can be arbitrarily used intact or, if necessary, after mixing with fillers, excipients, binders, etc., and then shaped into various shapes such as granules, spheres, sticks, plates, cubes, etc.

In order to improve the elasticity and strength, various shaped products or their intermediates, containing the α-glucan mixture of the present invention, can be, if necessary, arbitrarily used in combination with other high molecular substances, other ingredients such as appropriate plasticizer and excipients, etc., which are generally used in the fields of foods, cosmetics, and pharmaceuticals. In the case of shaped products mainly composed of other excipients, the α-glucan mixture of the present invention can be used as an adhesive. An example of the excipient includes polysaccharides or derivatives thereof such as pullulan, carrageenan, xanthan gum, carboxymethyl cellulose, cellulose, hemicelluloses, gum arabic, guar gum, pectin, chitin, agarose, dextrin, amylose, and starch containing processed starch; and proteins such as gelatin and casein; and saccharides such as sorbitol, mannitol, maltitol, sucrose, maltose, lactose, α,α-trehalose, α,β-trehalose, gum arabic, corn starch, and crystalline cellulose; and inorganic substances such as aluminum hydroxide, calcium hydroxide, magnesium hydroxide, barium hydroxide, calcium sulfate, calcium sulfite, calcium carbonate, silica, calcium silicate, basic magnesium carbonate, kaolin, and talc. Particularly, α,α-trehalose can be advantageously used as a stabilizer because it inhibits the deterioration of effective ingredients due to their oxidative decomposition and has functions of stably retaining the activity of the effective ingredients. Polyalcohols such as sorbitol, maltitol, α,α-trehalose, glycerol, polyvinyl alcohol, polyethylene glycol, and propylene glycol can be used as a plasticizer.

The α-glucan mixture of the present invention can be advantageously used as a food material. The use of the α-glucan mixture into a food is not particularly restricted, and α-glucan mixture can be used for a molded snack, molded cheese, molded dry fruit, fish meat molded product, fish egg molded product, and fish meat food, meat food, pseudo meat food, molded food, and the like by utilizing the binding properties. Also, it can be used as a food loosening agent, a pressure-sensitive adhesive for food, a processed rice, or the like by using the film-forming (coating) property.

In addition, the α-glucan mixture of the present invention can be used for improving the texture and improving the preservability of foods by incorporating into a bread, confectionery, and noodle. As a preferable example of using the α-glucan mixture of the present invention, the α-glucan mixture can be made into a dough by mixing with other materials such as flour, salt (sodium chloride), sugar (sucrose), and water; and kneading them; and the resulting dough can be shaped and cooked to make into foods. When the α-glucan mixture of the present invention is incorporated into foods for producing dough, the amount of α-glucan mixture to be incorporated is, usually, 20% by weight or lower, preferably, 10% by weight or lower, and more preferably, 5% by weight or lower, on a dry solid basis. Since the α-glucan mixture of the present invention is produced by using waxy starch as a material, it can be used for imparting textures such as moist texture, chewy texture, soft texture, a good mouthfeel, crispy texture to a bread, confectionery, and noodle.

The α-glucan mixture of the present invention can be used for confectionery produced by preparing dough and then baking, steaming, frying or drying dough. Such confectionery includes Japanese confectionery such as steamed filled dumplings, rice cake, rice cracker, dumpling, Turkish delight, a bean-jam pancake, Kintsuba, Imagawa-yaki; Western confectionery such as biscuit, cookie, cracker, wafer, sponge cakes (roll cake, sponge cake), butter cakes (pound cake, madeleine, gateau chocolate, financier), cream puff, Baumkuchen, muffin, souffle, pie, and tart; and Chinese confectionery such as mooncake.

The α-glucan mixture of the present invention can be used for noodle products, for example, noodles such as Japanese noodles, Chinese noodle, and buckwheat noodles; pastas such as spaghetti, linguine, bucatini, fettuccine, penne, conchiglie, and macaroni; and skin for wonton, meat and vegetable dumpling, and steamed meat dumpling.

As described above, the α-glucan mixture of the present invention has both satisfactory solubility in water and satisfactory high strength when made into films or the like; and contains α-glucan having the molecular weight in a prescribed range. Therefore, by using the α-glucan mixture for producing a shaped product, it can be expected that the shaped product is imparted constant strength, dissolution rate, and disintegration rate. Accordingly, the α-glucan mixture of the present invention can be used for foods, cosmetics, and pharmaceuticals and quasi-drugs, requiring a constant in vivo dynamics of effective ingredients. The α-glucan mixture of the present invention can be used for shaped products such as film, sheet, capsule, microcapsule, gauze, fiber for surgical string, etc. Also, it can be used as an excipient, adhesive or coating agent for preparing tablets granules, and solid formulations when dissolved at use.

When a shaped product is produced by using the α-glucan mixture at least as a part of material, various ingredients widely used in respective fields can be appropriately added to the α-glucan mixture of the present invention In the cases of the above shaped products are cosmetics or their intermediates, they can be made into, for example, pack, mask, bath preparation, or mouth-refreshing film, and one or more of the following ingredients can be appropriately added alone or in combination to the above shaped products: Antiseptics such as paraoxybenzoic acid, benzalkonium chloride, and pentanediol; skin whitening agents such as albutin, ellagic acid, tetrahydrocurcuminoid, and vitamin P; anti-inflammatories such as glycyrrhizic acid and glycyrrhiza extract; cell activators such as lactoferrin, chondroitin sulfate, hyaluronic acid, KANKOSO-101, and KANKOSO-301; humectants such as elastin, keratin, urea, and ceramide; oil-based medicines such as squalane, petrolatum, and tri-2-ethyl hexanoic acid cetyl; and water-soluble high molecules such as carrageenan, carboxymethyl cellulose, locust bean gum, and carboxy vinyl polymer; and alcohols such as 1,3-butylene glycol, polyethylene glycol, propylene glycol, sorbitol, and maltitol.

In the cases of the above shaped products are pharmaceuticals, quasi-drugs, or intermediates thereof, they can be formulated into granules, tablets, sugar-coated tablets, etc., and one or more of the following ingredients can be appropriately added alone or in combination to the above formulated products: Immunosuppresants such as azathioprine, cyclosporine, cyclophosphamide, methotrexate, tacrolimus hydrate, and busulfan; anticancer agents such as capecitabine, rituximab, trastuzumab, bevacizumab, docetaxel, imatinib mesylate, 5-fluorouracil, anastrozole, taxol, tamoxifen, docetaxel, and hydroxycarbamide; anti-viral agents such as abacavir sulfate, zalcitabine, didanosine, famciclovir, and ribavirin; antibiotics such as amoxicillin, talampicillin, cefixime, sulfamethizole, levofloxacin hydrate, cefcapene pivoxil hydrochloride hydrate, cefditoren pivoxil, and clarithromycin; antipyretic-analgesics such as acetaminophen, aspirin, ethenzamide, and methyl salicylate; steroids such as prednisolone, dexamethasone, and betamethasone; proteins or peptides such as interferon-α, interferon-β, insulin, oxytocin, and somatropin; biological drugs such as BCG vaccine, Japanese encephalitis vaccine, measles vaccine, polio vaccine, vaccine, tetanus toxoid, habu antitoxin, and human immunoglobulin; vitamin preparations and derivatives thereof such as retinol, thiamine, riboflavin, pyridoxine, cyanocobalamin, L-ascorbic acid, carotenoid, ergosterol, tocopherol, biotin, calcitonin, Coenzyme Q, α-lipoic acid, nicotinic acid, menaquinone, ubiquinone, and pyrroloquinone quinoline; and crude drug extracts such as Korean ginseng extract, aloe extract, propolis extract, glycyrrhiza extract, cinnamon extract, and *Swertia japonica* extract.

The α-glucan mixture of the present invention can also be used as a material of industrial products. "Industrial products" as referred to as in the present specification includes agricultural chemicals, fertilizer, feed, paper construction, polishing agent, adhesives (binder), gelling agent, paint, dye, colorant, ink, detergent, toiletry-product, biodegradable resin (bioplastic), and gas barrier resin. For example, in the field of agricultural chemicals and fertilizer, the α-glucan mixture of the present invention can be used as an excipient for granulating or tableting agricultural chemicals and fertilizer. For example, in the papermaking field, the α-glucan mixture of the present invention can be used as a surface coating agent or reinforcing agent for the paper construction product by using the binding property and film-forming property, and also used as a material for anonwoven fabric or and packaging material. Further, the α-glucan mixture of the present invention can be used as an alternative of polyvinyl alcohol (PVA) and carboxymethyl cellulose (CMC), and as a binder for gypsum board, cement, and battery separator.

The following experiments explain the present invention in detail:

Experiment 1: Preparation of Various α-Glucan Mixtures Different in the Degree of Hydrolysis Using Waxy Starch as a Material Various α-glucan mixtures different in the degree of hydrolysis were prepared by using a waxy corn starch as a waxy starch, and their physical properties were investigated.

"Waxy Corn Starch Y", a commercially available waxy corn starch commercialized by J-Oil Mills, Inc., Tokyo, Japan, was suspended in deionized water to give a solid concentration of 30% by weight, admixed with calcium chloride to give a solid concentration of 0.1% by weight, and then adjusted to pH 6.0 to make into a waxy corn starch suspension. The waxy corn starch suspension was admixed with "Spitase HK", a product name of a thermostable α-amylase specimen commercialized by Nagase ChemteX Corporation, Osaka, Japan, in an amount of zero, 0.001, 0.002, 0.004, 0.008 or 0.02% by weight per solid waxy corn starch, and gelatinized and liquefied by heating at pH 6.5 and 100° C. for 20 min, and then heated at 140° C. for 30 min to stop the hydrolytic reaction. The resulting hydrolyzates were respectively decolored by using activated charcoal, deionized using ion-exchange resins, and filtrated using a membrane filter. The resulting filtrates were subjected to spray-drying using a NIRO disk-type spray-dryer, commercialized by GEA Process Engineering K.K, Tokyo Japan, using the conditions of inlet temperature of 205° C., outlet temperature of 103° C., air volume of 12.4 m³/min, disk rotation speed of 18,000 rpm and material feeding speed of 23 kg/hour, and about 2 kg each of powdery α-glucan mixtures were prepared and named Test Samples 1 to 6, respectively.

About 20 mg each of Test Samples 1 to 6 was subjected to gel-filtration HPLC conducted under the following conditions and Mw and Mn of each test sample were measured, and then Mw/Mn was calculated. Mw and Mn of Test Samples were determined by analyzing those chromatograms using a software for molecular weight distribution based on a calibration curve which is prepared based on gel-filtration chromatograms of pullulan standards for molecular weight determination, commercialized by Hayashibara Co., Ltd. (Conditions for gel-filtration HPLC)

Column: "TSK GEL α-M", commercialized by Tosoh Corporation, Tokyo, Japan; (two columns were connected in series)
Eluent: 10 mM sodium phosphate buffer (pH 7.0);
Flow rate: 0.3 mL/min;
Column temperature: 40° C.
Detector: "RID 10A", a refractive index detector, commercialized by Shimadzu Corporation, Kyoto, Japan;
Software: "LC Solution GPC Software", a software for data analysis, commercialized by Shimadzu Corporation, Kyoto, Japan.

Also, DEs of Test Samples 1 to 6 were measured as an index of the degree of hydrolysis. Further, solubility in cold water of Test Sample 1 to 6 were judged respectively by dissolving them into deionized water to give a solid concentration of 30% by weight. Test Samples 1 to 6 were respectively made into aqueous solutions with solid concentration of 30% by weight and the viscosities of the resulting solutions were measured at 35° C. by using "Model MCR102", a dynamic viscoelasticity rheometer, commercialized by Anton Paar Japan K.K., Tokyo, Japan. The viscosity of an aqueous solution with a solid concentration of 30% by weight was expressed by shear viscosity under the conditions at 35° C. and shear rate of 10.8/sec. The results are in Table 1.

TABLE 1

| | Test Sample (α-Glucan Mixture) No. | | | | | |
|---|---|---|---|---|---|---|
| | 1 | 2 | 3 | 4 | 5 | 6 |
| Amount of α-amylase (% by weight/starch) | 0 | 0.001 | 0.002 | 0.004 | 0.008 | 0.02 |
| Mw (kDa) | Unmeasurable*1 | 2,560 | 1,080 | 373 | 183 | 39.1 |
| Mn (kDa) | Unmeasurable*1 | 335 | 134 | 75.8 | 46.3 | 1.08 |
| Mw/Mn | Unmeasurable*1 | 7.63 | 8.09 | 4.92 | 3.95 | 35.9 |
| Dextrose Equivalent (DE) | 0.07 | 0.06 | 0.17 | 0.34 | 0.62 | 1.03 |
| Solubility in cold water | No | Passable | Passable | Passable | Passable | Passable |
| Viscosity of 30% (w/w) aqueous solution (mPa · s) | 26,700 | 2,330 | 1,070 | 457 | 220 | 57 |

*1Unable to subject to gel-filtration HPLC analysis.

As shown in Table 1, in the case of Test Sample 1, obtained by simply gelatinizing waxy corn starch without using thermostable α-amylase, the gelatinized solution with a solid concentration of 30% by weight showed a relatively high viscosity, 26,700 mPa·s, and its handling was difficult. Mw and Mn of the solution could not be measured because the viscosity of the solution was high and the pre-treatment for subjecting the sample to the molecular distribution analysis by gel-filtration HPLC could not be carried out. Further, Test Sample 1 was inferior in solubility in water and not dissolved in cold water.

In the cases of Test Samples 2 to 5, prepared by using relatively low amounts of thermostable α-amylase, the degree of hydrolysis of the gelatinized waxy corn starch was increased with the increase of the amount of amylase. In addition, Mw, Mn, and Mw/Mn were lowered with the increase of the amount of amylase. Test Samples 2 to 5 showed Mw in a range of 2,560 to 183 kDa and Mw/Mn in a range of 3.95 to 8.09, and showed solubility in cold water. The viscosities of aqueous solutions with solid concentrations of 30% by weight, prepared by using Test Sample 2 to 5, were lowered to be 2,330 to 220 mPa·s, with increase of the amount of amylase, i.e., with increase of the degree of hydrolysis. While, Test Sample 6 showed a relatively low Mw of 39.1 kDa and a relatively high value of Mw/Mn of 35.9.

Experiment 2: Applicability of Various α-Glucan Mixtures as a Material of an Edible Film Each of Test Samples 1 to 6, obtained in Experiment 1, was used as a material and made into a film without adding any plasticizer. Then, the applicability of each α-glucan mixture as a material of an edible film (suitability as a film) was investigated by evaluating the characteristics of the above film.

A film was prepared by the steps of dissolving each of Test Samples 1 to 6, obtained in Experiment 1, homogeneously in deionized water to give a solid concentration of 30% by weight, defoaming by centrifuging at 3,000 rpm for 10 min, pouring and spreading the suitable amount of the solution on a polyethylene terephthalate (PET) sheet using "Model YBA", a baker applicator commercialized by Yoshimitsu Seiki, Japan, and drying at an ambient temperature for one night or longer. Test Sample 6 showed poor film formability and was hardly made into a film due to the relatively low viscosity of the aqueous solution. On the other hand, Test Samples 1 to 5 showed satisfactory film formability and were made into films with a thickness of about 40 mm. The resulting films were called to Film Samples 1 to 5, respectively.

The suitability as a film of Film Sample 1 to 5 was evaluated to the following two types by observing the appearance with eyes:

Passable: Good film with a uniform thickness and smooth surface;
No: Film with an uneven thickness and uneven surface.

Also, the transparency of each film was evaluated to the following two types by observing with eyes:

Passable: Transparent;
No: Cloudy.

Further, the solubility in water of each film was evaluated to the following 2 types by the steps of adding a film cut to 1 cm square size to 200 ml deionized water kept at 30° C., and measuring the elapsed time for completely dissolving the film in water by the observing with eyes under a stirring condition:

Passable: Completely dissolved by stirring within 1 min;
No: Not completely dissolved by stirring within 1 min;
The results are in Table 2.

In addition, 10 circular pieces with a diameter of 20 mm were cut out from Film Samples 1 to 5, respectively, and the 10 pieces were subjected to aforesaid piercing test for rupture strength and the average rupture strength of piercing of each film sample were calculated. The results are also shown in Table 2.

As shown in Table 2, Film Sample 1, prepared by using Test Sample 1 which was obtained by simply gelatinizing waxy corn starch, was a film with uneven surface and lacked transparency. Although Film Sample 1 showed a relatively high rupture strength of piercing, 2.66 N/mm$^2$, it was not completely dissolved in the above solubility test and was inferior in solubility in water. While, Film Samples 2 to 5 were those with uniform thickness and smooth surface, showing good transparency and solubility in water. The values of rupture strength of piercing of Film Samples 2 to 5 were relatively high to be 2.0 N/mm$^2$. As described above, since Test Sample 6 was hardly made into a film, Film Sample 6 could not be obtained.

As described above, it was revealed that Test Samples 2 to 5 had applicability as a material for preparing a satisfactory edible film without using any plasticizer. On the other hand, Test Samples 1 and 6 lacked the applicability.

From the results in Experiments 1 and 2, it was concluded that α-glucan mixture, having Mw in a range of 150 kDa to 3,000 kDa and Mw/Mn of less than 10, obtained by partially hydrolyzing waxy starch by allowing amylase to act on it, had characteristics of showing satisfactory solubility in cold water and keeping adequate viscosity. It was also revealed that an edible film with a uniform, transparency, and satisfactory solubility in water, showing the rupture strength of piercing of 2.0 N/mm$^2$ or higher, can be obtained by making the α-glucan mixture into a film.

Experiment 3: Preparation of α-Glucan Mixture Containing α-Glucan Having an Isomaltose Structure at the Non-Reducing End (Part 1)

In this experiment and the following Experiment 4, in order to provide more advantageous properties to the above α-glucan mixture, a saccharide-transferring enzyme was allowed to act on an α-glucan mixture and various α-glucan mixtures containing α-glucan having an isomaltose structure at the non-reducing end were prepared.

Except for using 0.002% by weight/solid of waxy corn starch of "Spitase HK", a thermostable α-amylase commercialized by Nagase ChemteX Corporation, Osaka, Japan, a solution containing α-glucan mixture was prepared by the same method in Experiment 1. To the resulting solution containing α-glucan mixture, 0.25, 0.5, 2.5, 10, or 25 units/g-solid of α-glucan mixture of a purified specimen of α-glucosyltransferase (hereinafter, may be abbreviated as "α-GTase" in this specification) derived from *Bacillus circulans* PP710, disclosed in WO2008/136331 applied for by the same applicant of the present invention, was added, incubated at pH 6.0 and 50° C. for 24 hours, and then stopped the enzyme reaction by heating at 140° C. for 10 min. Each reaction mixture was purified by the same method in Experiment 1 and subjected to spray-drying using NIRO

TABLE 2

| Properties of film | Film Sample No. | | | | | |
|---|---|---|---|---|---|---|
| | 1 | 2 | 3 | 4 | 5 | 6 |
| Film thickness (μm) | 50 | 40 | 40 | 40 | 40 | Unmeasurable*2 |
| Aptitude (Appearance) | No | Passable | Passable | Passable | Passable | No |
| Transparency | No | Passable | Passable | Passable | Passable | Unmeasurable*2 |
| Solubility in water | No | Passable | Passable | Passable | Passable | Unmeasurable*2 |
| Rupture strength of piercing (N/mm$^2$) | 2.66 | 2.95 | 2.67 | 2.73 | 2.39 | Unmeasurable*2 |

*2Unable to make into a film because of its low viscosity.

disk-type spray-dryer, commercialized by GEA Process Engineering K.K, Tokyo Japan, and about 2 kg each of powdery α-glucan mixtures were prepared and named Test Samples 7 to 11, respectively.

As in Experiment 1, Mw, Mn, and Mw/Mn of Test Samples 7 to 11 were determined. Also, in order to evaluate the content of α-glucan having an isomaltose structure at the non-reducing end, 1% (w/v) aqueous solution of each Test Samples 7 to 11 was subjected to the aforesaid IDase digestion test and the isomaltose content of the resulting digest was measured. Further, similarly with Experiment 1, DE, solubility in cold water, the viscosity of aqueous solution with a solid concentration of 30% by weight, prepared by each Test Sample, were evaluated. In addition, the tolerance for retrogradation of Test Samples 7 to 11 were evaluated. The tolerance for retrogradation was evaluated to the following 2 types by storing each aqueous solution with a solid concentration of 30% by weight at 6° C. for one-week:

No: White turbidity caused by the retrogradation is detected in the aqueous solution at one-week storage;
  Passable: Transparency of the aqueous solution is kept at one-week storage.

The results are in Table 3. The results for Test Sample 3, prepared in Experiment 1 by adding 0.002% by weight/solid of waxy corn starch of the thermostable α-amylase to waxy corn starch suspension, are also shown in Table 3 as control data.

were varied. The viscosities of aqueous solutions with solid concentrations of 30% by weight, prepared by using Test Sample 7 to 11, were in a range of 990 to 651 mPa·s and slightly lower than that of Test Sample 3, but no significant change was observed. Among Test Samples 7 to 11, Test Sample 7 showed no tolerance for retrogradation because its aqueous solution showed the white turbidity in the tolerance test for retrogradation of keeping an aqueous solution with solid concentration of 30% by weight at 6° C. for one-week. On the other hand, it was revealed that Test Samples 8 to 11 had remarkable tolerance for retrogradation of keeping transparent aqueous solution at the one-week storage in the same test.

Experiment 4: Preparation of α-Glucan Mixture Containing α-Glucan Having an Isomaltose Structure at the Non-Reducing End (Part 2)

Various α-glucan mixtures containing α-glucan having an isomaltose structure at the non-reducing end were prepared by using an α-glucan mixture having a lower Mw than that used in Experiment 3 as a material, and their properties were investigated as in Experiment 3.

Except for using 0.004% by weight/solid of waxy corn starch of thermostable α-amylase, an α-glucan mixture having a lower molecular weight was prepared by the same method in Experiment 1. To the resulting α-glucan mixture, 0.5, 1.0, 2.5, or 5.0 10 units/g-solid of α-glucan mixture of

TABLE 3

| | Test sample (α-Glucan Mixture) No. | | | | | |
|---|---|---|---|---|---|---|
| | 3 | 7 | 8 | 9 | 10 | 11 |
| Amount of α-amylase (% by weight/starch) | 0.002 | 0.002 | 0.002 | 0.002 | 0.002 | 0.002 |
| Amount of α-GTase (units/g-sample) | 0 | 0.25 | 0.5 | 2.5 | 10 | 25 |
| Mw (kDa) | 1,080 | 1,290 | 1,370 | 1,450 | 1,320 | 1,210 |
| Mn (kDa) | 134 | 90.2 | 96.2 | 62.8 | 37.5 | 19.4 |
| Mw/Mn | 8.09 | 14.3 | 14.2 | 23.2 | 35.1 | 62.3 |
| Isomaltose content in IDase digest (% by weight) | 0 | 1.57 | 3.83 | 17.2 | 21.8 | 25.4 |
| Dextrose Equivalent (DE) | 0.17 | 0.30 | 0.35 | 0.93 | 2.00 | 5.30 |
| Solubility in cold water | Passable | Passable | Passable | Passable | Passable | Passable |
| Viscosity of 30% (w/w) aqueous solution (mPa · s) | 1,070 | 990 | 998 | 829 | 684 | 651 |
| Tolerance for retrogradation of 30% (w/w) aqueous solution | No | No | Passable | Passable | Passable | Passable |

As shown in Table 3, in the cases of Test Samples 7 to 11 obtained by the steps of allowing 0.002% by weight of thermostable α-amylase to act on waxy corn starch and further allowing α-GTase to act on the resultant, it was confirmed that isomaltose in an amount of 1.57% by weight to 25.4% by weight, on a dry solid basis of the digest, was formed by IDase digestion. Accordingly, it was confirmed that, although varying in the content, Test Samples 7 to 11 were α-glucan mixtures containing α-glucan having an isomaltose structure at the non-reducing end.

In the cases of Test Samples 7 to 11, the Mw/Mn (Degree of dispersion) of Test Sample was increased with the increase of the amount of α-GTase, and particularly, in the case of Test Sample 11, prepared by using 25 units/g-substrate, which was the maximum amount of α-GTase, the Mw/Mn was increased to 62.3. Although Test Samples 7 to 11 were not so different from Test Sample 3 in Mw, those Mw/Mw were apparently increased and revealed that the molecular weights of molecules in those α-glucan mixtures a purified specimen of α-GTase derived from *Bacillus circulans* PP710 was added as in Experiment 1, incubated at pH 6.0 and 50° C. for 24 hours, and then stopped the enzyme reaction by heating at 140° C. for 10 min. Each reaction mixture was purified by the same method in Experiment 3 and subjected to spray-drying using NIRO disk-type spray-dryer, commercialized by GEA Process Engineering K.K, Tokyo Japan, and about 2 kg each of powdery α-glucan mixtures were prepared and named Test Samples 12 to 15, respectively.

As in Experiment 3, Mw, Mn, Mw/Mn, isomaltose content in the IDase digest, and DE of Test Samples 12 to 15 were determined. Solubility in cold water, the viscosity of aqueous solution with a solid concentration of 30% by weight, and the tolerance for retrogradation of Test Samples 12 to 15 were also evaluated. The results are in Table 4. The results for Test Sample 4, prepared in Experiment 1 by adding 0.004% by weight/solid of waxy corn starch of the thermostable α-amylase to waxy corn starch suspension, are also shown in Table 4 as control data.

TABLE 4

| | Test sample (α-Glucan Mixture) No. | | | | |
|---|---|---|---|---|---|
| | 4 | 12 | 13 | 14 | 15 |
| Amount of α-amylase (% by weight/starch) | 0.004 | 0.004 | 0.004 | 0.004 | 0.004 |
| Amount of α-GTase (units/g-sample) | 0 | 0.5 | 1.0 | 2.5 | 5.0 |
| Mw (kDa) | 373 | 449 | 430 | 397 | 365 |
| Mn (kDa) | 75.8 | 54.0 | 32.6 | 17.6 | 9.74 |
| Mw/Mn | 4.92 | 8.3 | 13.2 | 22.6 | 37.5 |
| Isomaltose content in IDase digest (% by weight) | 0.00 | 1.50 | 4.57 | 12.7 | 20.6 |
| Dextrose Equivalent (DE) | 0.34 | 0.46 | 0.81 | 1.64 | 2.76 |
| Solubility in cold water | Passable | Passable | Passable | Passable | Passable |
| Viscosity of 30% (w/w) aqueous solution (mPa·s) | 457 | 525 | 433 | 348 | 294 |
| Retrogradation-tolerance of 30% (w/w) aqueous solution | No | No | Passable | Passable | Passable |

As shown in Table 4, in the cases of Test Samples 12 to 15 obtained by the steps of allowing 0.004% by weight of thermostable α-amylase to act on waxy corn starch and further allowing α-GTase to act on the resultant, it was confirmed that isomaltose in an amount of 1.5% by weight to 20.6% by weight, on a dry solid basis of the digest, was formed by IDase digestion. Accordingly, it was confirmed that Test Samples 12 to 15 were α-glucan mixtures containing α-glucan having an isomaltose structure at the non-reducing end as in the cases of Test Sample 7 to 11.

Mw of Test Sample 12 to 15 were in a range of 449 to 365 kDa and the values were about one third of those of Test Sample 7 to 11. Therefore, it was confirmed that Test Sample 12 to 15 were α-glucan mixtures having relatively lower molecular weight. The Mw/Mn of Test Samples 12 to 15 were in a range of 8.3 to 37.5. Although Test Samples 12 to 15 were not so different from Test Sample 4 in Mw, those Mw/Mw were apparently increased with the increase of the amount of α-GTase. The DE of Test Samples 12 to 15 were in a range of 0.45 to 2.76. The viscosities of aqueous solutions with solid concentrations of 30% by weight, prepared by using Test Sample 12 to 15, were in a range of 525 to 294 mPa·s and not so different from that of Test Sample 4 prepared without using α-GTase. Among Test Samples 12 to 15, Test Sample 12 showed no tolerance for retrogradation because its aqueous solution showed the white turbidity in the tolerance test for retrogradation of keeping an aqueous solution with solid concentration of 30% by weight at 6° C. for one week as in the case of Test Sample 4. On the other hand, it was revealed that Test Samples 13 to 15 had remarkable tolerance for retrogradation of keeping transparent aqueous solution at the one-week storage in the same test.

From the results in Experiments 3 and 4, it was revealed that Test Samples 7 and 12, which showed relatively low isomaltose content of 1.57% by weight or 1.50% by weight/solid of IDase digest, i.e., which had relatively low content of α-glucan having an isomaltose structure at the non-reducing end, showed no tolerance for retrogradation. It was also revealed that Test Samples 8 to 11 and 13 to 15, which showed isomaltose content of 3.83% by weight or higher/solid of IDase digest, showed tolerance for retrogradation. Accordingly, the above results indicate that the tolerance for retrogradation can be provided to α-glucan mixture with keeping the properties of material by allowing α-GTase to act on α-glucan mixture to form a certain amount of α-glucan having an isomaltose structure at the non-reducing end.

Experiment 5: Applicability of α-Glucan Mixture Containing α-Glucan Having an Isomaltose Structure at the Non-Reducing End as a Material of Edible Film Test Samples 7 to 15, obtained in Experiments 3 and 4, were used as materials and made into films with a thickness of about 40 to 50 μm by the same method in Experiment 2, respectively, and the resulting films were named to Film Samples 7 to 15. Successively, appearance (aptitude for film), transparency, solubility in water, and rupture strength of piercing of Film Samples 7 to 15 were evaluated by the same method in Experiment 2. The results of Film Samples 7 to 11, prepared by using α-glucan mixture having Mw of 1,210 kDa or higher as materials, are in Table 5. The results of Film Samples 12 to 15, prepared by using α-glucan mixture having Mw of less than 500 kDa as materials, are in Table 6.

TABLE 5

| | Film Sample No. | | | | | |
|---|---|---|---|---|---|---|
| Properties of film | 3 | 7 | 8 | 9 | 10 | 11 |
| Film thickness (μm) | 40 | 41 | 45 | 40 | 47 | Unmeasurable*3 |
| Aptitude (Appearance) | Passable | Passable | Passable | Passable | Passable | No |
| Transparency | Passable | Passable | Passable | Passable | Passable | Passable |
| Solubility in water | Passable | Passable | Passable | Passable | Passable | Passable |
| Rupture strength of piercing (N/mm$^2$) | 2.67 | 3.12 | 3.93 | 3.25 | 3.80 | Unmeasurable*3 |

*3 Unable to obtain the value because the film is very fragile.

TABLE 6

| | Film Sample No. | | | | |
|---|---|---|---|---|---|
| Properties of film | 4 | 12 | 13 | 14 | 15 |
| Film thickness (μm) | 40 | 40 | 40 | 40 | Unmeasurable*3 |
| Aptitude (Appearance) | Passable | Passable | Passable | Passable | No |
| Transparency | Passable | Passable | Passable | Passable | Passable |
| Solubility in water | Passable | Passable | Passable | Passable | Passable |
| Rupture strength of piercing (N/mm$^2$) | 2.73 | 3.24 | 2.66 | 2.03 | Unmeasurable*3 |

*3 Unable to obtain the value because the film is very fragile.

As shown in Table 5, Film Samples 7 to 10, prepared from α-glucan mixture containing α-glucan having an isomaltose structure at the non-reducing end and having Mw of 1,210 kDa or higher, showed advantageous properties of good transparency and solubility in water, and the rapture strength for piercing of 2.0 N/mm² as in the case of Film Sample 3, prepared by using an α-glucan mixture obtained by partially hydrolyzing waxy corn starch by using amylase. However, Film Sample 11, prepared from Test Sample 11, i.e., α-glucan mixture where the Mw/Mn was increased to 62.3 by the action of α-GTase, was very fragile and hard to make into a film.

Further, as shown in Table 6, Film Samples 12 to 14, prepared from α-glucan mixture containing α-glucan having an isomaltose structure at the non-reducing end and having Mw of less than 500 kDa, showed advantageous properties of good transparency and solubility in water, and the rapture strength of piercing of 2.0 N/mm² as in the case of Film Sample 4, prepared by using an α-glucan mixture obtained by partially hydrolyzing waxy corn starch by using amylase. However, Film Sample 15, prepared from Test Sample 15, i.e., α-glucan mixture where the Mw/Mn was increased to 37.5 by the action of α-GTase, was very fragile and hard to make into a film.

From the results in Experiments 3, 4, and 5, it was revealed that α-glucan mixture having a remarkable tolerance for retrogradation can be obtained by the steps of allowing amylase to act on gelatinized waxy corn starch to form α-glucan mixture and allowing α-GTase to act on the resulting α-glucan mixture to form α-glucan having an isomaltose structure at the non-reducing end and showing isomaltose content in the IDase digest of 3% by weight or higher. Considering the results in Experiments 1 and 2 and the results in Experiments 3, 4, and 5, a film, showing good transparency and solubility in water, rupture strength of piercing of 2.0 N/mm² or higher and being hard to crack, can be obtained without adding any plasticizer by using α-glucan mixture, having Mw in a range of 150 kDa to 3,000 kDa and Mw/Mn of 35.1 or lower, as a material.

Reference Experiment 1: Comparison with Pullulan, Roasted Starch and Dextrin

Pullulan, roasted starch, and dextrin were selected to be compared with α-glucan mixture of the present invention and those properties were investigated by the same method in Experiment 1. Further, films were prepared by using them as materials without adding any plasticizer as in Experiments 2 and 5, and the respective properties were investigated.

"PULLULAN", a commercially available pullulan commercialized by Hayashibara Co., Ltd., Okayama, Japan, and "PINEDEX #100", a commercially available dextrin commercialized by Matsutani Chemical Industry Co., Ltd., Hyogo, Japan, were used as pullulan and dextrin, respectively. A roasted starch was prepared by the following method: An aqueous solution, obtained by dissolving magnesium chloride hexahydrate into 110 mL of water to give a concentration of 0.008 mole/kg, was admixed with 500 g of a commercially available waxy corn starch, and further mixed in a mortar for about 30 min to obtain a wet mixture. The wet mixture was spread on a stainless container to give a thickness of about 1 cm, and heated for 3 hours in an air-circulation type incubator controlled to 135° C., and then a roasted sample was obtained. The resulting roasted sample was suspended in water to give a concentration of 30% by weight and gelatinized by using "RVA-4", a rapid viscoanalyzer, commercialized by Newport Scientific Inc., Maryland, USA, at 90° C. with stirring at 160 rpm for 15 min to make into a roasted starch. Pullulan, the roasted starch, and dextrin were respectively made into a film by the same method in Experiment 2, and the properties of the resulting films were evaluated by the same method in Experiment 2. The results are in Table 7.

TABLE 7

| | | Pullulan | Roasted starch | Dextrin |
|---|---|---|---|---|
| Characteristics of glucan | Mw (kDa) | 399 | 1,170 | 114 |
| | Mn (kDa) | 10.6 | 27.9 | 8.4 |
| | Mw/Mn | 37.8 | 41.9 | 13.5 |
| | Dextrose Equivalent (DE) | 1.86 | 0.25 | 3.63 |
| | Viscosity of 30% (w/w) aqueous solution (mPa · s) | 35,700 | 1,490 | 87 |
| | Retrogradation-tolerance of 30% (w/w) aqueous solution (stored at 6° C. for one week) | Passable | No | No |
| Properties of film | Film thickness (μm) | 40 | 40 | Unmeasurable*4 |
| | Aptitude (Appearance) | Passable | Passable | Unmeasurable*4 |
| | Transparency | Passable | Passable | Unmeasurable*4 |
| | Solubility in water | Passable | Passable | Unmeasurable*4 |
| | Rupture strength of piercing (N/mm²) | 3.03 | 1.55 | Unmeasurable*4 |

*4Unable to make into a film.

As shown in Table 7, pullulan showed Mw of 399 kDa and the Mw/Mn of 37.8. The viscosity of the aqueous solution with a solid concentration of 30% by weight, prepared from pullulan, was relatively high to be 35,700 mPa·s and there was a problem that the aqueous solution was hardly handled. However, the aqueous solution did not cause the difficulty to make into a film, and the formed film with a thickness of 40 μm showed a relatively large strength, a rapture strength of piercing of 3.03 N/mm².

The roasted starch showed Mw of 1,170 kDa, which is in the same level of Test Sample 7 to 10 obtained in Experiment 3, and a relatively high Mw/Mn of 41.9. The aqueous solution with a solid concentration of 30% by weight, prepared from the roasted starch showed no tolerance for retrogradation. The film with a thickness of 40 μm, obtained by using the roasted starch, showed a relatively small strength, a rapture strength of piercing of 1.55 N/mm².

In the case of the dextrin, the viscosity of the aqueous solution with a solid concentration of 30% by weight, prepared from the dextrin, was relatively low to be 87 mPa·s. Although we tried to make into a film from the dextrin, the resultant showed an extreme fragility and, substantially, could not make into a film.

From the results of Experiments 1 to 5 and Reference Experiment 1, it was revealed that the α-glucan mixture of the present invention, i.e., the α-glucan mixture, which is obtainable by a process comprising the steps of gelatinizing waxy starch and liquefying the gelatinized waxy starch by allowing an amylase to act on it, and has the following characteristics (1) and (2):

(1) having Mw in a range of 150 kDa to 3,000 kDa; and (2) having the value of dividing Mw with Mn, Mw/Mn, of 35.1 or lower; can be used equivalently to pullulan, widely used as a material of edible film, because it can be used as a material of edible film having advantageous transparency, solubility in water, and strength.

Reference Experiment 2: Amylose Content of α-Glucan Mixture

The amylose contents of "Waxy Corn Starch Y", a waxy corn starch commercialized by J-Oil Mills, Inc., Tokyo, Japan, which was used as the material of α-glucan mixture in Experiments 1, 3, and 4, and the α-glucan mixture, obtained in the following Example 4, i.e., an α-glucan mixture having Mw of 566 kDa, Mw/Mn of 13.2, the isomaltose content in the IDase digest of 7.0% by weight, were respectively measured and compared with each other. Also, the amylose contents of "Showa Corn Starch", a commercially available corn starch commercialized by Shikishima Starch MFG. Co., Ltd., Mie, Japan, and "Starch from Corn", code No. S4180, a commercially available high amylose corn starch commercialized by Sigma-Aldrich Japan, Tokyo, Japan, were measured as references.

As described above, the amylose content of each sample was measured based on a color reaction of amylose and iodine, according to the method for measuring amylose content described in the standard measurement method in Notice No. 332 of Ministry of Agriculture, Forestry and Fisheries. In this Experiment, "Potato Amylose Type II" a reagent grade amylose commercialized by Sigma-Aldrich Japan, Tokyo, Japan, was used for preparing standard amylose solutions and a calibration curve was prepared. The results are in Table 8.

TABLE 8

| Sample | Amylose content (% by weight) |
|---|---|
| Waxy corn starch | 13.4 |
| α-Glucan mixture obtained in Example 4 | 10.3 |
| Corn starch | 35.9 |
| High amylose corn starch | 46.9 |

As shown in Table 8, the amylose contents (% by weight) of waxy corn starch and α-glucan mixture obtained in Example 4 were determined to be 13.4% by weight and 10.3% by weight by the measurement method, respectively. While, those of commercially available corn starch and high amylose corn starch were determined to be 35.9% by weight and 46.9% by weight, respectively. Generally, the amylose content has been known to be high in the order of high amylose corn starch, corn starch, and waxy corn starch. It was revealed that the above results supported the conventional knowledge.

The α-glucan mixture of the present invention was produced by the process of partially hydrolyzing waxy starch by the amylase, or the process of partially hydrolyzing waxy starch by the amylase and successively allowing α-GTase to act on the resulting partial hydrolyzate to form α-glucan having an isomaltose structure at the non-reducing end. Different from the case of a starch-debranching enzyme, both the amylase and α-GTase are not able to hydrolyze a branching structure of waxy starch, bound via α-1,6 linkage. Therefore, linear amylose is not formed from waxy starch by the actions of the amylase and α-GTase, and the amylose content of the reaction product is never increased. Accordingly, the fact that the α-glucan mixture of the present invention showed an amylose content equal or lower than waxy corn starch in the measurement indicates that the α-glucan mixture of the present invention was produced by using waxy corn starch as the material. In other words, it can be judged that an α-glucan mixture, having Mw of 150 kDa or higher and showing an amylose content of less than 15% by weight by the measurement, is produced by the process comprising the steps of gelatinizing waxy starch and liquefying the resulting gelatinized waxy starch by allowing amylase to act on it, or the process comprising the steps of gelatinizing waxy starch, liquefying the resulting gelatinized waxy starch by allowing amylase to act on it, and further allowing α-GTase to act on the resulting liquefied waxy starch.

The present invention will be explained in more detail based on the following Examples but it should never be restricted thereby.

Example 1

"Waxy corn starch Y", a commercially available waxy corn starch manufactured by J-Oil Mills, Inc., Tokyo, Japan, is suspended in deionized water to give a solid concentration of 30% by weight, admixed with calcium chloride to give a concentration of 0.1% by weight, and then adjusted to pH 6.0 to make into a waxy corn starch suspension. "Spitase HK", a thermostable α-amylase manufactured by Nagase ChemteX Corporation, Osaka, Japan, was added to the waxy starch suspension to give a concentration of 0.002% by weight per solid-waxy corn starch, and gelatinized and liquefied by heating at 100° C. for 20 min, and then the reaction was stopped by heating at 140° C. for 10 min, and dried at 135° C. by subjecting to a drum dryer. The dried product was pulverized by passing through a pulverizer to make into a powdery α-glucan mixture.

The α-glucan mixture showed Mw of 980 kDa, the Mw/Mn of 7.9, and showed a solubility in cold water, and the viscosity of the aqueous solution with a concentration of 30% by weight of 960 mPa·s. The product can be advantageously used as a material of edible films, and as a thickener, binder, etc., for foods, cosmetics, pharmaceuticals, and industrial products.

Example 2

"Waxy Corn Starch Y", a commercially available waxy corn starch manufactured by J-Oil Mills Inc., Tokyo, Japan, was suspended in deionized water to give a solid concentration of 35% by weight, admixed with calcium chloride to give a concentration of 0.1% by weight, and adjusted to pH 6.0 to make into a waxy corn starch suspension. "Termamyl 60L", a thermostable α-amylase manufactured by Novozymes Japan Ltd., Chiba, Japan, was added to the waxy starch suspension to give a concentration of 0.004% per solid-waxy corn starch, and gelatinized and liquefied by heating at 100° C. for 20 min, and then the reaction was stopped by heating at 140° C. for 15 min, and dried by subjecting to a spray dryer using a conventional method to make into a powdery α-glucan mixture.

The α-glucan mixture showed Mw of 351 kDa, the Mw/Mn of 4.6, and showed a solubility in cold water, and the viscosity of the aqueous solution with a concentration of 30% by weight of 445 mPa·s. The product can be advantageously used as a material of edible films, and as a thickener, binder, etc., for foods, cosmetics, pharmaceuticals, and industrial products.

Example 3

Except for gelatinizing and liquefying "Waxy Corn Starch Y", a commercially available waxy corn starch manufactured by J-Oil Mills Inc., Tokyo, Japan, admixing 1.0 unit/g-starch of α-GTase derived from *Bacillus circulans* PP710 disclosed in WO2008/136331, and allowing to act at pH 6.0, 50° C. for 24 hours, the same procedure in Example 1 was carried out. As a result, a powdery α-glucan mixture containing α-glucan having an isomaltose structure at the non-reducing end was obtained.

The α-glucan mixture showed Mw of 1,270 kDa, the Mw/Mn of 22.1, and showed a solubility in cold water, and the viscosity of the aqueous solution with a concentration of 30% by weight of 896 mPa·s. The isomaltose content in the digest obtained by allowing IDase to act on the α-glucan mixture was 9.3% by weight. The α-glucan mixture was that containing α-glucan having an isomaltose structure at the non-reducing end, and showed a tolerance for retrogradation, showing no white turbidity by storing for one week when the α-glucan mixture was subjected to a test for tolerance for retrogradation by keeping the aqueous solution with a solid concentration of 30% by weigh at 6° C. for one-week. The product can be advantageously used as a material of edible films, and as a thickener, binder, etc., for foods, cosmetics, pharmaceuticals, and industrial products.

Example 4

Except for gelatinizing and liquefying "Waxy Corn Starch Y", a commercially available waxy corn starch manufactured by J-Oil Mills Inc., Tokyo, Japan, by the same method in Example 2, admixing 1.0 unit/g-starch of α-GTase derived from *Bacillus circulans* PP710 disclosed in WO2008/136331, and allowing to act at pH 6.0, 50° C. for 20 hours, the same procedure in Example 1 was carried out. As a result, a powdery α-glucan mixture containing α-glucan having an isomaltose structure at the non-reducing end was obtained.

The α-glucan mixture showed Mw of 566 kDa, the Mw/Mn of 13.2, and showed a solubility in cold water, and the viscosity of the aqueous solution with a concentration of 30% by weight of 483 mPa·s. The isomaltose content in the digest obtained by allowing IDase to act on the α-glucan mixture was 7.0% by weight. The α-glucan mixture was that containing α-glucan having an isomaltose structure at the non-reducing end, and showed a tolerance for retrogradation, showing no white turbidity by storing for one week when the α-glucan mixture was subjected to a test for tolerance for retrogradation by keeping the aqueous solution with a solid concentration of 30% by weigh at 6° C. for one-week. The product can be advantageously used as a material of edible films, and as a thickener, binder, etc., for foods, cosmetics, pharmaceuticals, and industrial products.

Example 5

Except for replacing the waxy corn starch to a waxy rice starch, gelatinizing and liquefying, and then admixing 2.5 units/g-starch of α-GTase derived from *Arthrobacter globiformis* PP349 disclosed in WO2008/136331, and allowing to act at pH 6.0, 50° C. for 24 hours, the same procedure in Example 2 was carried out. As a result, a powdery α-glucan mixture containing α-glucan having an isomaltose structure at the non-reducing end was obtained.

The α-glucan mixture showed Mw of 1,360 kDa, the Mw/Mn of 22.4, and showed a solubility in cold water, and the viscosity of the aqueous solution with a concentration of 30% by weight of 840 mPa·s. The isomaltose content in the digest obtained by allowing IDase to act on the α-glucan mixture was 17.5% by weight. The α-glucan mixture was that containing α-glucan having an isomaltose structure at the non-reducing end, and showed a tolerance for retrogradation, showing no white turbidity by storing for one week when the α-glucan mixture was subjected to a test for tolerance for retrogradation by keeping the aqueous solution with a solid concentration of 30% by weigh at 6° C. for one week. The product can be advantageously used as a material of edible films, and as a thickener, binder, etc., for foods, cosmetics, pharmaceuticals, and industrial products.

Example 6

<Edible Film>

The α-glucan mixture obtained in Example 1 was suspended in deionized water and stirred to make into a solution with a solid concentration of 30% by weight, and then the solution was defoamed under a reduced pressure. The film was cast on a PET film and dried at a temperature of 35° C. and a relative humidity of 33%, an edible film containing an α-glucan mixture, having a thickness of 80 μm, was obtained. Since the obtained edible film contained 5.2% by weight of water, and showed a high strength against the breaking stress, a good water solubility, and a stable dissolution rate with little variation for each production lot, it can be advantageously used for foods, cosmetics, pharmaceuticals, etc.

Example 7

<Edible Film>

The α-glucan mixture obtained in Example 2 is suspended in deionized water and stirred to make into a solution with a solid concentration of 25% by weight, and then the solution was defoamed under a reduced pressure. The film was cast on a PET film and dried at a temperature of 35° C. and a relative humidity of 33%, an edible film containing an α-glucan mixture, having a thickness of 60 μm, was obtained. Since the obtained edible film contained 4.6% by weight of water, and showed a high strength against the breaking stress, a good water solubility, and a stable dissolution rate with little variation for each production lot, it can be advantageously used for foods, cosmetics, pharmaceuticals, etc.

Example 8

<Edible Film>

The α-glucan mixture containing α-glucan having an isomaltose structure at the non-reducing end, obtained in Example 3, was suspended in deionized water and stirred to make into a solution with a solid concentration of 30% by weight, and then the solution was defoamed under a reduced pressure. The film was cast on a PET film and dried at a temperature of 35° C. and a relative humidity of 33%, an edible film containing an α-glucan mixture, having a thickness of 50 μm, was obtained. Since the obtained edible film contained 4.1% by weight of water, and showed a high strength against the breaking stress, a satisfactory water solubility, and a stable dissolution rate with little variation for each production lot, it can be advantageously used for foods, cosmetics, pharmaceuticals, etc.

Example 9

<Edible Film>

The α-glucan mixture containing α-glucan having an isomaltose structure at the non-reducing end, obtained in Example 4, is suspended in deionized water and stirred to make into a solution with a solid concentration of 25% by weight, and then the solution was defoamed under a reduced pressure. The film was cast on a PET film and dried at a temperature of 35° C. and a relative humidity of 33%, an edible film containing an α-glucan mixture, having a thickness of 50 μm, was obtained. Since the obtained edible film contained 4.8% by weight of water, and showed a high strength against the breaking stress, a good water solubility, a stable dissolution rate with little variation for each production lot, it can be advantageously used for foods, cosmetics, pharmaceuticals, etc.

Example 10

<Mouth Refreshing Film>

According to the conventional method, 69.25 parts by weight of deionized water, 22 parts by weight of α-glucan mixture prepared by the method in Example 1, 1 part by weight of carrageenan, 0.15 part by weight of xanthan gum, 0.15 part by weight of locust bean gum, 0.8 part by weight of maltitol, 3 parts by weight of "HAYASHIBARA HESPERIDIN S" (glycosyl hesperidin commercialized by Hayashibara, Co., Ltd., Okayama, Japan), 2.6 parts by weight of emulsified mint oil, 0.3 part by weight of sucralose, and 0.25 part by weight of citric acid were dissolved by mixing at 90° C. for 3 hours, homogeneously casting on a 2×10 m stainless-steel plate and drying at 60° C. for 4 hours, a thickness of about 200 μm, a width of approximately 200 cm, and a length of 10 m, water content of approximately 8%, a film product having a mass of approximately 2.2 g per 100 cm$^2$ was obtained. The product was cut to 1×2 cm, 20 sheets and filled in a portable case to make into a mouth refreshing film.

Since the product was an edible mouth refreshing film having moderate strength and rapidly dissolving property in the mouth, and contained a glycosyl hesperidin, it can be used for the purpose of maintaining and promoting an oral health. Since the product was produced by using the α-glucan mixture of the present invention, having an almost constant saccharide composition with small variation by the lot, as a material, it was an edible film which showed a constant dissolution rate in the mouth and stable dissolution rate of effective ingredients such as glucosyl-hesperidin.

Example 11

<Loosening Improving Agent for Noodles>

Ten parts by weight of the α-glucan mixture prepared in Example 1 was dissolved into 90 parts by weight of deionized water to make into a loosening improving agent for noodles. After boiling noodles and lightly removing water by boiling basket, 5 parts by weight of the loosening improving agent for noodles was mixed with 100 parts by weight of boiled noodles. The resulting noodle was put into a plastic container (80 mm×70 mm×45 mm of height) and stored at 6° C. for 48 hours, and then the loosening property of the noodle after the storage was evaluated. The noodles of which surface was treated with the loosening improvement agent containing the α-glucan mixture, was compared with a control noodles which had not been sprayed with the agent. The noodles did not show stickiness to each other, and showed no incongruity in taste and texture. The noodles treated with the α-glucan mixture had a gloss on the surface of the noodles, and had excellent appearance.

Example 12

<Adhesive for Foods>

The adhesive for food was prepared by dissolving 5 parts by weight of the α-glucan mixture, prepared by Example 2, into 95 parts by weight of deionized water. A bread dough ball 45 g (diameter 8 cm) for a cooked bun was coated with 0.2 g of an adhesive for food by using a brush. Sesame was added to the surface of the bread dough ball, and then the bread dough ball was treated to final fermentation (at 35° C., relative humidity of 80%, for 50 min), and baked (upper temperature: 185° C., lower temperature: 180° C., for 9 min) to make into a bun. The bun prepared by using the food adhesive and the control bun were compared. The amount of peeled sesame was remarkably reduced in the case of the bun prepared by using the adhesive for food, and the adhesiveness of the adhesive for food was good.

Example 13

<Coating Film>

An aqueous solution was prepared by dissolving one part by weight of the α-glucan mixture containing α-glucan having an isomaltose structure at the non-reducing end, prepared by Example 3, and 0.2 part by weight of a gum arabic into 100 parts by weight of water. A fresh egg within 10 hours after egg-laying was immersed in this aqueous solution containing the α-glucan mixture for 30 sec, and dried at a temperature of 30° C. for 2 hours to form the coating film containing the α-glucan mixture.

The eggs with the coating film formed by the α-glucan mixture were stored at room temperature (15 to 25° C.), and the edible period was compared with the control non-treated egg (without a coating film). As a result, in the edible period of the eggs in which the coating film was formed with the α-glucan mixture, was extended to about five times of that of the non-treated egg (without a coating film). The α-glucan mixture coating film can be advantageously used for storing an egg used as a material for food industry.

Example 14

<Solid Adhesive>

A mixture of 7 parts by weight of α-glucan mixture, obtained by the method of Example 2, 30 parts by weight of dimethyl sulfoxide, 25 parts by weight of water, 3 parts by weight of pullulan, and 2 parts by weight of dibenzylidene xylitol were dissolved by stirring at 90° C. for one hour. The resultant solution was injected into a lipstick-type cylindrical container, 14 mm in diameter and 50 mm in height, having a mechanism capable of lifting up and down the content, and cooled to obtain a solid adhesive. The product was uniformly spreadable over a craft paper when applied thereon, and sufficient in the initial binding capacity. The solidity was less influenced by the change of an ambient temperature, and this exerted a satisfactory spreadability and binding capacity.

Example 15

<Tablet>

According to conventional manner, 450 parts by weight of ethenzamide, 300 parts by weight of acetaminophen, 50 parts by weight of caffeine, 25 parts by weight of maltitol, 25 parts by weight of α,α-trehalose, 200 parts by weight of sucrose, 400 parts by weight of xylitol, 500 parts by weight of corn starch, 20 parts by weight of polyethylene glycol, six parts by weight of α-glucan mixture containing α-1,4-glucan having isomaltose structure at the non-reducing end obtained by the method of Example 4, and six parts by weight of gum arabic, one part by weight of "αG-SWEET", a product name of α-glucosyl stevioside commercialized by Toyo Sugar Refining Co., Ltd., Tokyo, Japan, were admixed and kneaded with 40 ml of water and tableted with a tableting machine to obtain a tablet (about 300 mg/tablet).

Since the product does not induce any cracking when tableted, has an adequate strength, and has a satisfactory water solubility, it can be used as a sublingual-type cold medicine that is injectable while dissolving in the mouth. The adhesive force inherent to the particulate composition containing pullulan is roughly constant because the product is produced with the particulate composition containing pullulan of the present invention as a material that retains the saccharide composition in such a manner of being less varied batch-by-batch and roughly consistent. By tableting the prescribed ingredients under constant conditions, a satisfactory tablet, which has a usually-stable shape and strength, can be obtained. Since the product has a constant dissolution rate in the mouth, the dissolution rates of the effective ingredients such as ethenzamide and acetaminophen are stable and they can be allowed to act on the body at a higher efficiency.

Example 16

<Fertilizer in Pile Shape>

Seventy parts by weight of mixed fertilizer (N=14%, $P_2O_5$=8%, $K_2O$=12%), 10 parts by weight of α-glucan mixture containing α-1,4-glucan having an isomaltose structure at the non-reducing end, obtained by the method of Example 3, 15 parts by weight of calcium sulfate and 5 parts by weight of water were sufficiently mixed and shaped by a extruder (L/D=20, compression ratio=1.8, the diameter of the die=30 mm) by heating at 80° C. to give a fertilizer in pile shape.

The product is so easy to be used that a fertilizer-container is unnecessary. The product possesses adequate strength for thick application and the releasing rate of the ingredients can be regulated by altering the compounding ratio. If necessary, a phytohormone, an agricultural agent, and a soil-improving agent can be easily mixed in the fertilizer in pile shape.

INDUSTRIAL APPLICABILITY

As described above, since the α-glucan mixture of the present invention has an appropriate molecular weight range, a satisfactory solubility in cold water, an appropriate viscosity, it can be used in various fields such as foods, cosmetics, pharmaceuticals, and industrial products without restriction. Further, among foods, particularly, the α-glucan mixture of the present invention can be preferably used as a material of edible films, a binder of the food materials, a texture-improving agent for bread and confectionery, a loosening improving agent for noodles and the like, and a storage stability improving agent, etc.

The invention claimed is:

1. An α-glucan mixture, which is obtainable by a process comprising the steps of gelatinizing waxy starch and liquefying the resulting gelatinized waxy starch by allowing an amylase to act on it, having the following characteristics (1) to (3):
   (1) having the weight average molecular weight (Mw) in a range of 150 kDa to 3,000 kDa;
   (2) having the value of dividing weight average molecular weight (Mw) with number average molecular weight (Mn), Mw/Mn, of 35.1 or lower; and
   (3) forming a hydrolyzate with isomaltose content of less than 22% by weight, on a dry solid basis of the hydrolyzate, when digested by isomaltodextranase (EC 3.2.1.94).

2. The α-glucan mixture of claim 1, which contains a-glucan having an isomaltose structure at the non-reducing end.

3. The α-glucan mixture of claim 2, wherein said α-glucan mixture forms isomaltose in an amount of over 3% by weight but less than 22% by weight, on a dry solid basis of the hydrolyzate, when digested by isomaltodextranase (EC 3.2.1.94).

4. The α-glucan mixture of claim 3, wherein said waxy starch is waxy corn starch.

5. The α-glucan mixture of claim 3, which further has the following characteristic:
   a film obtained by steps of molding the α-glucan mixture without plasticizer and drying, with a thickness of 40 to 50 mu.m, exhibits a rupture strength of piercing of 2.0 $N/mm^2$ or higher when analyzed on a piercing test for rupture strength using an adaptor with a sectional area of 1 $mm^2$.

6. The α-glucan mixture of claim 3, which can be made into a homogeneous solution when dissolved into water by admixing with deionized water to give a solid concentration of 20% by weight and stirring at 30° C. for 15 min.

7. An edible film, which is obtainable by steps of molding the α-glucan mixture of claim 3, without adding any plasticizer and drying and exhibits a rupture strength of piercing of 2.0 $N/mm^2$ or higher when analyzed on a piercing test for rupture strength using an adaptor with a sectional area of 1 $mm^2$.

8. The α-glucan mixture of claim 2, wherein said waxy starch is waxy corn starch.

9. The α-glucan mixture of claim 2, which further has the following characteristic:
   a film obtained by steps of molding the α-glucan mixture without plasticizer and drying, with a thickness of 40 to 50 mu.m, exhibits a rupture strength of piercing of 2.0 $N/mm^2$ or higher when analyzed on a piercing test for rupture strength using an adaptor with a sectional area of 1 $mm^2$.

10. The α-glucan mixture of claim 2, which can be made into a homogeneous solution when dissolved into water by admixing with deionized water to give a solid concentration of 20% by weight and stirring at 30° C. for 15 min.

11. An edible film, which is obtainable by steps of molding the α-glucan mixture of claim 2, without adding any plasticizer and drying and exhibits a rupture strength of piercing of 2.0 $N/mm^2$ or higher when analyzed on a piercing test for rupture strength using an adaptor with a sectional area of 1 $mm^2$.

12. The α-glucan mixture of claim 1, wherein said waxy starch is waxy corn starch.

13. The α-glucan mixture of claim 1, which further has the following characteristic:
   a film obtained by steps of molding the a-glucan mixture without plasticizer and drying, with a thickness of 40 to 50 mu.m, exhibits a rupture strength of piercing of 2.0 $N/mm^2$ or higher when analyzed on a piercing test for rupture strength using an adaptor with a sectional area of 1 $mm^2$.

14. The α-glucan mixture of claim 1, which can be made into a homogeneous solution when dissolved into water by admixing with deionized water to give a solid concentration of 20% by weight and stirring at 30° C. for 15 min.

15. A process for producing the α-glucan mixture of claim 1, comprising the steps of:
gelatinizing waxy starch by heating a waxy starch suspension with a solid concentration of 20% by weight; and
forming α-glucan mixture having the weight average molecular weight (Mw) in a range of 150 kDa to 3,000 kDa by allowing an amylase to act on the resulting gelatinized waxy starch.

16. The process of claim 15, further comprising a step of allowing an α-glucosyltransferase, which acts on starch hydrolyzate and catalyzes α-1,6 transglucosylation reaction to the non-reducing end of the starch hydrolyzate, to act on the formed α-glucan mixture.

17. The process of claim 16, wherein said α-glucosyltransferase is derived from a microorganism of the genus *Bacillus* or *Arthrobacter* and has the following characteristics (A) to (F):
(A) Action
Acting on maltose and/or α-1,4 glucan having a glucose polymerization degree of 3 or higher, catalyzing mainly α-1,4 transglucosylation reaction and α-1,6 transglucosylation reaction, and transferring glucose to the C-4 or C-6 hydroxyl group of the glucose residue at the non-reducing end;
(B) Molecular weight
90,000±10,000 daltons on SDS-polyacrylamide gel electrophoresis;
(C) Optimum temperature
About 50° C. when reacted at pH 6.0 for 30 min;
(D) Optimum pH
About pH 6.0 when reacted at 40° C. for 30 min;
(E) Thermal stability
Stable up to the temperature of 40° C. when incubated at pH 6.0 for 60 min; and
(F) pH stability
Stable in the range of pH 4.0 to 8.0 when incubated at 4° C. for 24 hours.

18. An edible film, which is obtainable by the steps of molding the α-glucan mixture of claim 1, without adding any plasticizer and drying and exhibits a rupture strength of piercing of 2.0 N/mm$^2$ or higher when analyzed on a piercing test for rupture strength using an adaptor with a sectional area of 1 mm$^2$.

* * * * *